(12) United States Patent
Goode

(10) Patent No.: US 12,053,626 B2
(45) Date of Patent: Aug. 6, 2024

(54) SURFACE ELECTRODES

(71) Applicant: EndoStim, Inc., Dallas, TX (US)

(72) Inventor: Paul V. Goode, Round Rock, TX (US)

(*) Notice: Subject to any disclaimer, the term of this patent is extended or adjusted under 35 U.S.C. 154(b) by 304 days.

(21) Appl. No.: 15/939,879

(22) Filed: Mar. 29, 2018

(65) Prior Publication Data

US 2019/0105491 A1   Apr. 11, 2019

Related U.S. Application Data

(60) Provisional application No. 62/482,588, filed on Apr. 6, 2017.

(51) Int. Cl.
*A61N 1/05* (2006.01)

(52) U.S. Cl.
CPC ......... *A61N 1/0517* (2013.01); *A61N 1/0509* (2013.01); *A61N 1/0558* (2013.01)

(58) Field of Classification Search
CPC .... A61N 1/0558; A61N 1/0553; A61N 1/059; A61N 2001/0582
See application file for complete search history.

(56) References Cited

U.S. PATENT DOCUMENTS

| | | | |
|---|---|---|---|
| 3,909,883 A | 10/1975 | Fegen | |
| 3,910,281 A | 10/1975 | Kletschka | |
| 4,393,883 A | 7/1983 | Smyth | |
| 4,414,986 A | 11/1983 | Dickhudt | |
| 4,612,934 A | 9/1986 | Borkan | |
| 4,735,205 A | 4/1988 | Chachques | |
| 5,117,827 A | 6/1992 | Stuebe | |
| 5,188,104 A | 2/1993 | Wernicke | |
| 5,193,539 A | 3/1993 | Schulman | |
| 5,197,491 A | 3/1993 | Anderson | |
| 5,231,988 A | 8/1993 | Wernicke | |
| 5,263,480 A | 11/1993 | Wernicke | |
| 5,292,344 A | 3/1994 | Douglas | |
| 5,360,428 A | 11/1994 | Hutchinson, Jr. | |
| 5,423,872 A | 6/1995 | Cigaina | |
| 5,531,778 A | 7/1996 | Maschino | |
| 5,540,730 A | 7/1996 | Terry, Jr. | |
| 5,556,425 A | 9/1996 | Hewson | |
| 5,606,242 A | 2/1997 | Hull | |

(Continued)

FOREIGN PATENT DOCUMENTS

| | | | |
|---|---|---|---|
| CN | 1476339 | | 2/2004 |
| CN | 105641805 | * | 2/2016 |
| CN | 105641805 A | | 6/2016 |
| EP | 1004330 | | 5/2000 |

(Continued)

OTHER PUBLICATIONS

International Search Report for PCT/US2018/025092, Jun. 27, 2018.

(Continued)

*Primary Examiner* — George R Evanisko
(74) *Attorney, Agent, or Firm* — Novel IP

(57) ABSTRACT

An implantable electrical lead for use in the stimulation of biological tissues is provided. The lead has at least one surface electrode comprising a distal end and a proximal end. The at least one surface electrode is placed on the surface of tissue at an implant site, and at least one anchoring element with a distal end and a proximal end for holding the electrode at a desired position on the implant site is placed above the electrode at the implant site.

13 Claims, 8 Drawing Sheets

(56) References Cited

U.S. PATENT DOCUMENTS

| | | |
|---|---|---|
| 5,633,573 A | 5/1997 | van Phuoc |
| 5,649,902 A | 7/1997 | Yoon |
| 5,674,205 A | 10/1997 | Pasricha |
| 5,690,691 A | 11/1997 | Chen |
| 5,697,375 A | 12/1997 | Hickey |
| 5,709,224 A | 1/1998 | Behl |
| 5,716,385 A | 2/1998 | Mittal |
| 5,716,392 A | 2/1998 | Bourgeois |
| 5,769,881 A | 6/1998 | Schroeppel |
| 5,810,810 A | 9/1998 | Tay |
| 5,836,994 A | 11/1998 | Bourgeois |
| 5,861,014 A | 1/1999 | Familoni |
| 5,861,044 A | 1/1999 | Crenshaw |
| 5,882,340 A | 3/1999 | Yoon |
| 5,893,883 A | 4/1999 | Torgerson |
| 5,935,126 A | 8/1999 | Riza |
| 5,995,872 A | 11/1999 | Bourgeois |
| 6,006,755 A | 12/1999 | Edwards |
| 6,026,326 A | 2/2000 | Bardy |
| 6,041,258 A | 3/2000 | Cigaina |
| 6,051,017 A | 4/2000 | Loeb |
| 6,091,992 A | 7/2000 | Bourgeois |
| 6,097,984 A | 8/2000 | Douglas |
| 6,216,039 B1 | 4/2001 | Bourgeois |
| 6,221,039 B1 | 4/2001 | Durgin |
| 6,243,607 B1 | 6/2001 | Mintchev |
| 6,254,598 B1 | 7/2001 | Edwards |
| 6,285,897 B1 | 9/2001 | Kilcoyne |
| 6,321,124 B1 | 11/2001 | Cigaina |
| 6,360,130 B1 | 3/2002 | Duysens |
| 6,381,495 B1 | 4/2002 | Jenkins |
| 6,449,511 B1 | 9/2002 | Mintchev |
| 6,510,332 B1 | 1/2003 | Greenstein |
| 6,542,776 B1 | 4/2003 | Gordon |
| 6,571,127 B1 | 5/2003 | Ben-Haim |
| 6,587,719 B1 | 7/2003 | Barrett |
| 6,591,137 B1 | 7/2003 | Fischell |
| 6,606,523 B1 | 8/2003 | Jenkins |
| 6,611,715 B1 | 8/2003 | Boveja |
| 6,612,983 B1 | 9/2003 | Marchal |
| 6,615,084 B1 | 9/2003 | Cigaina |
| 6,678,561 B2 | 1/2004 | Forsell |
| 6,684,104 B2 | 1/2004 | Gordon |
| 6,735,477 B2 | 5/2004 | Levine |
| 6,749,607 B2 | 6/2004 | Edwards |
| 6,754,536 B2 | 6/2004 | Swoyer |
| 6,760,626 B1 | 7/2004 | Boveja |
| 6,820,019 B1 | 11/2004 | Kelly |
| 6,826,428 B1 | 11/2004 | Chen |
| 6,832,114 B1 | 12/2004 | Whitehurst |
| 6,853,862 B1 | 2/2005 | Marchal |
| 6,876,885 B2 | 4/2005 | Swoyer |
| 6,879,859 B1 | 4/2005 | Boveja |
| 6,879,861 B2 | 4/2005 | Benz |
| 6,901,295 B2 | 5/2005 | Sharma |
| 6,915,165 B2 | 7/2005 | Forsell |
| 6,947,792 B2 | 9/2005 | Ben-Haim |
| 6,952,613 B2 | 10/2005 | Swoyer |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,127,295 B2 | 10/2006 | Evans |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,203,551 B2 | 4/2007 | Houben |
| 7,255,675 B2 | 8/2007 | Gertner |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,363,084 B2 | 4/2008 | Kurokawa |
| 7,444,183 B2 | 10/2008 | Knudson |
| 7,477,994 B2 | 1/2009 | Sunshine |
| 7,499,752 B2 | 3/2009 | Maschino |
| 7,519,431 B2 | 4/2009 | Goetz |
| 7,519,433 B2 | 4/2009 | Foley |
| 7,558,629 B2 | 7/2009 | Keimel |
| 7,593,777 B2 | 9/2009 | Gerber |
| 7,599,736 B2 | 10/2009 | DiLorenzo |
| 7,620,454 B2 | 11/2009 | Dinsmoor |
| 7,664,551 B2 | 2/2010 | Cigaina |
| 7,676,270 B2 | 3/2010 | Imran |
| 7,702,394 B2 | 4/2010 | Imran |
| 7,702,395 B2 | 4/2010 | Towe |
| 7,702,934 B2 | 4/2010 | Imran |
| 7,711,437 B1 | 5/2010 | Bornzin |
| 7,720,539 B2 | 5/2010 | Mintchev |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,809,442 B2 | 10/2010 | Bolea |
| 7,813,809 B2 | 10/2010 | Strother |
| 7,835,796 B2 | 11/2010 | Maschino |
| 7,848,802 B2 | 12/2010 | Goetz |
| 7,890,185 B2 | 2/2011 | Cohen |
| 7,899,540 B2 | 3/2011 | Maschino |
| 7,914,468 B2 | 3/2011 | Shalon |
| 7,941,221 B2 | 5/2011 | Foley |
| 7,957,807 B2 | 6/2011 | Starkebaum |
| 7,962,214 B2 | 6/2011 | Byerman |
| 7,983,755 B2 | 7/2011 | Starkebaum |
| 8,135,470 B2 | 3/2012 | Keimel |
| 8,155,758 B2 | 4/2012 | Roline |
| 8,160,709 B2 | 4/2012 | Soffer |
| 8,185,206 B2 | 5/2012 | Starkebaum |
| 8,282,561 B2 | 10/2012 | Towe |
| 8,380,321 B2 | 2/2013 | Goetz |
| 8,406,868 B2 | 3/2013 | Buschman |
| 8,423,134 B2 | 4/2013 | Buschman |
| 8,447,403 B2 | 5/2013 | Sharma |
| 8,447,404 B2 | 5/2013 | Sharma |
| 8,452,407 B2 | 5/2013 | Whitehurst |
| 8,467,874 B2 | 6/2013 | Chen |
| 8,467,884 B2 | 6/2013 | Chen |
| 8,521,292 B2 | 8/2013 | Wei |
| 8,538,532 B2 | 9/2013 | Starkebaum |
| 8,538,534 B2 | 9/2013 | Soffer |
| 8,543,210 B2 | 9/2013 | Sharma |
| 8,556,952 B2 | 10/2013 | Shadduck |
| 8,594,811 B2 | 11/2013 | Chen |
| 8,712,529 B2 | 4/2014 | Sharma |
| 8,712,530 B2 | 4/2014 | Sharma |
| 8,718,771 B2 | 5/2014 | Gandhi |
| 8,761,903 B2 | 6/2014 | Chen |
| 8,792,986 B2 | 7/2014 | Cigaina |
| 8,831,737 B2 | 9/2014 | Wesselink |
| 8,892,217 B2 | 11/2014 | Camps |
| 9,020,597 B2 | 4/2015 | Sharma |
| 9,037,245 B2 | 5/2015 | Sharma |
| 9,061,147 B2 | 6/2015 | Sharma |
| 9,345,879 B2 | 5/2016 | Sharma |
| 9,498,619 B2 | 11/2016 | Goode |
| 9,724,510 B2 | 8/2017 | Sharma |
| 2001/0041831 A1 | 11/2001 | Starkweather |
| 2002/0103522 A1 | 8/2002 | Swoyer |
| 2002/0138075 A1 | 9/2002 | Edwards |
| 2002/0161414 A1 | 10/2002 | Flesler |
| 2002/0165589 A1 | 11/2002 | Imran |
| 2003/0009202 A1 | 1/2003 | Levine |
| 2003/0014086 A1 | 1/2003 | Sharma |
| 2003/0028226 A1 | 2/2003 | Thompson |
| 2003/0055463 A1 | 3/2003 | Gordon |
| 2003/0078633 A1 | 4/2003 | Firlik |

(56) References Cited

U.S. PATENT DOCUMENTS

| | | |
|---|---|---|
| 2003/0120321 A1 | 6/2003 | Bumm |
| 2003/0144708 A1 | 7/2003 | Starkebaum |
| 2003/0195600 A1 | 10/2003 | Tronnes |
| 2004/0010290 A1 | 1/2004 | Schroeppel |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0088033 A1 | 5/2004 | Smits |
| 2004/0116977 A1 | 6/2004 | Finch |
| 2004/0138586 A1 | 7/2004 | Ganz |
| 2004/0147976 A1 | 7/2004 | Gordon |
| 2004/0167583 A1 | 8/2004 | Knudson |
| 2004/0172088 A1 | 9/2004 | Knudson |
| 2004/0186544 A1 | 9/2004 | King |
| 2004/0193229 A1 | 9/2004 | Starkebaum |
| 2004/0215287 A1 | 10/2004 | Swoyer |
| 2004/0236381 A1 | 11/2004 | Dinsmoor |
| 2004/0236382 A1 | 11/2004 | Dinsmoor |
| 2004/0243182 A1 | 12/2004 | Cohen |
| 2005/0027328 A1 | 2/2005 | Greenstein |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131485 A1 | 6/2005 | Knudson |
| 2005/0131486 A1 | 6/2005 | Boveja |
| 2005/0137480 A1 | 6/2005 | Alt |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0222638 A1 | 10/2005 | Foley |
| 2005/0245788 A1 | 11/2005 | Gerber |
| 2005/0251219 A1 | 11/2005 | Evans |
| 2006/0004304 A1 | 1/2006 | Parks |
| 2006/0015162 A1 | 1/2006 | Edward |
| 2006/0036293 A1 | 2/2006 | Whitehurst |
| 2006/0041277 A1 | 2/2006 | Deem |
| 2006/0047323 A1 | 3/2006 | Foley |
| 2006/0064037 A1 | 3/2006 | Shalon |
| 2006/0074459 A1 | 4/2006 | Flesler |
| 2006/0089699 A1 | 4/2006 | Imran |
| 2006/0095077 A1 | 5/2006 | Tronnes |
| 2006/0106442 A1 | 5/2006 | Richardson |
| 2006/0116736 A1 | 6/2006 | DiLorenzo |
| 2006/0122660 A1 | 6/2006 | Boveja |
| 2006/0149337 A1 | 7/2006 | John |
| 2006/0167498 A1 | 7/2006 | DiLorenzo |
| 2006/0200217 A1 | 9/2006 | Wessman |
| 2006/0206160 A1 | 9/2006 | Cigaina |
| 2006/0218011 A1 | 9/2006 | Walker |
| 2006/0247717 A1 | 11/2006 | Starkebaum |
| 2006/0247718 A1 | 11/2006 | Starkebaum |
| 2006/0247719 A1 | 11/2006 | Maschino |
| 2006/0247721 A1 | 11/2006 | Maschino |
| 2006/0247722 A1 | 11/2006 | Maschino |
| 2006/0265021 A1 | 11/2006 | Herbert |
| 2006/0270989 A1 | 11/2006 | McMichael |
| 2007/0016274 A1 | 1/2007 | Boveja |
| 2007/0049793 A1 | 3/2007 | Ignagni |
| 2007/0060955 A1 | 3/2007 | Strother |
| 2007/0060968 A1 | 3/2007 | Strother |
| 2007/0060979 A1 | 3/2007 | Strother |
| 2007/0066995 A1 | 3/2007 | Strother |
| 2007/0067000 A1 | 3/2007 | Strother |
| 2007/0100388 A1 | 5/2007 | Gerber |
| 2007/0106337 A1 | 5/2007 | Errico |
| 2007/0106338 A1 | 5/2007 | Errico |
| 2007/0114971 A1 | 5/2007 | Uesaka |
| 2007/0142699 A1 | 6/2007 | Jandrall |
| 2007/0142831 A1 | 6/2007 | Shadduck |
| 2007/0142884 A1 | 6/2007 | Jandrall |
| 2007/0156182 A1 | 7/2007 | Castel |
| 2007/0162084 A1 | 7/2007 | Chen |
| 2007/0162085 A1 | 7/2007 | DiLorenzo |
| 2007/0179542 A1 | 8/2007 | Prakash |
| 2007/0185374 A1 | 8/2007 | Kick |
| 2007/0238942 A1 | 10/2007 | Baylor |
| 2007/0239248 A1 | 10/2007 | Hastings |
| 2007/0244375 A1 | 10/2007 | Jenkins |
| 2007/0255118 A1 | 11/2007 | Miesel |
| 2007/0255335 A1 | 11/2007 | Herbert |
| 2007/0255336 A1 | 11/2007 | Herbert |
| 2007/0255352 A1 | 11/2007 | Roline |
| 2007/0265662 A1 | 11/2007 | Ufford |
| 2007/0265666 A1 | 11/2007 | Roberts |
| 2007/0265668 A1 | 11/2007 | Reinke |
| 2007/0265671 A1 | 11/2007 | Roberts |
| 2007/0265674 A1 | 11/2007 | Olson |
| 2007/0282410 A1 | 12/2007 | Cross |
| 2007/0293910 A1 | 12/2007 | Strother |
| 2007/0299481 A1 | 12/2007 | Syed |
| 2008/0021512 A1 | 1/2008 | Knudson |
| 2008/0039904 A1 | 2/2008 | Bulkes |
| 2008/0046062 A1 | 2/2008 | Camps |
| 2008/0058836 A1 | 3/2008 | Moll |
| 2008/0058891 A1 | 3/2008 | Ben-Haim |
| 2008/0086179 A1 | 4/2008 | Sharma |
| 2008/0132968 A1 | 6/2008 | Starkebaum |
| 2008/0147137 A1 | 6/2008 | Cohen |
| 2008/0154191 A1 | 6/2008 | Gobel |
| 2008/0183238 A1 | 7/2008 | Chen |
| 2008/0195171 A1 | 8/2008 | Sharma |
| 2008/0208355 A1 | 8/2008 | Stack |
| 2009/0012421 A1 | 1/2009 | Bek |
| 2009/0018617 A1 | 1/2009 | Skelton |
| 2009/0018619 A1 | 1/2009 | Skelton |
| 2009/0020406 A1 | 1/2009 | Nirmalakhandan |
| 2009/0030475 A1* | 1/2009 | Brynelsen ............... A61N 1/05 607/40 |
| 2009/0069803 A1 | 3/2009 | Starkebaum |
| 2009/0076498 A1 | 3/2009 | Saadat |
| 2009/0088817 A1 | 4/2009 | Starkebaum |
| 2009/0131993 A1 | 5/2009 | Rousso |
| 2009/0132001 A1 | 5/2009 | Soffer |
| 2009/0187223 A1 | 7/2009 | Gross |
| 2009/0192564 A1 | 7/2009 | Armstrong |
| 2009/0204063 A1 | 8/2009 | Policker |
| 2009/0210019 A1 | 8/2009 | Kim |
| 2009/0264951 A1 | 10/2009 | Sharma |
| 2009/0281553 A1 | 11/2009 | Kalloo |
| 2010/0004648 A1 | 1/2010 | Edwards |
| 2010/0010388 A1 | 1/2010 | Panken |
| 2010/0049026 A1 | 2/2010 | Gerber |
| 2010/0057085 A1 | 3/2010 | Holcomb |
| 2010/0069789 A1 | 3/2010 | Hirota |
| 2010/0076345 A1 | 3/2010 | Soffer |
| 2010/0170812 A1 | 7/2010 | Odierno |
| 2010/0198039 A1 | 8/2010 | Towe |
| 2010/0228313 A1 | 9/2010 | Starkebaum |
| 2010/0268495 A1 | 10/2010 | Armstrong |
| 2010/0324432 A1 | 12/2010 | Bjoerling |
| 2010/0324644 A1 | 12/2010 | Levi |
| 2011/0004266 A1 | 1/2011 | Sharma |
| 2011/0034967 A1 | 2/2011 | Chen |
| 2011/0046653 A1 | 2/2011 | Addington |
| 2011/0071589 A1 | 3/2011 | Starkebaum |
| 2011/0213437 A9 | 9/2011 | Armstrong |
| 2011/0224665 A1 | 9/2011 | Crosby |
| 2011/0295335 A1 | 12/2011 | Sharma |
| 2011/0295336 A1 | 12/2011 | Sharma |
| 2011/0301662 A1 | 12/2011 | Bar-Yoseph |
| 2011/0307023 A1 | 12/2011 | Tweden |
| 2011/0307027 A1 | 12/2011 | Sharma |
| 2011/0307028 A1 | 12/2011 | Sharma |
| 2012/0232610 A1 | 9/2012 | Soffer |

(56) References Cited

U.S. PATENT DOCUMENTS

| | | |
|---|---|---|
| 2012/0232615 A1 | 9/2012 | Barolat |
| 2012/0259389 A1 | 10/2012 | Starkebaum |
| 2012/0265103 A1 | 10/2012 | Policker |
| 2012/0277619 A1 | 11/2012 | Starkebaum |
| 2012/0296166 A1 | 11/2012 | Kim |
| 2012/0310317 A1 | 12/2012 | Lund |
| 2013/0030503 A1 | 1/2013 | Yaniv |
| 2013/0035740 A1 | 2/2013 | Sharma |
| 2013/0072928 A1 | 3/2013 | Schaer |
| 2013/0090551 A1 | 4/2013 | Sharma |
| 2013/0178912 A1 | 7/2013 | Sharma |
| 2013/0218229 A1 | 8/2013 | Sharma |
| 2013/0231660 A1 | 9/2013 | Edwards |
| 2013/0238048 A1 | 9/2013 | Almendinger |
| 2014/0012348 A1 | 1/2014 | Starkebaum |
| 2014/0018657 A1 | 1/2014 | Sharma |
| 2014/0081366 A1 | 3/2014 | Bentley |
| 2014/0088664 A1 | 3/2014 | Sharma |
| 2014/0088666 A1 | 3/2014 | Goetz |
| 2014/0107726 A1 | 4/2014 | Voznesensky |
| 2014/0135886 A1 | 5/2014 | Cook |
| 2014/0194953 A1 | 7/2014 | Slavin |
| 2014/0222106 A1 | 8/2014 | Sharma |
| 2014/0228911 A1 | 8/2014 | Sharma |
| 2014/0243593 A1 | 8/2014 | Goode |
| 2014/0249594 A1 | 9/2014 | Sharma |
| 2014/0364678 A1 | 12/2014 | Harry |
| 2015/0045786 A1 | 2/2015 | Edwards |
| 2015/0057718 A1 | 2/2015 | Sharma |
| 2015/0119952 A1 | 4/2015 | Sharma |
| 2015/0224310 A1 | 8/2015 | Sharma |
| 2015/0360037 A1 | 12/2015 | Hahn |
| 2016/0001071 A1 | 1/2016 | Sharma |
| 2016/0015392 A1 | 1/2016 | Gettman |
| 2016/0045730 A1 | 2/2016 | Kim |
| 2016/0059010 A1 | 3/2016 | Sharma |
| 2017/0197028 A1 | 7/2017 | Goldsmith |
| 2017/0224986 A1 | 8/2017 | Imran |
| 2017/0348049 A1* | 12/2017 | Vrba ................ A61B 18/1492 |
| 2018/0154135 A1 | 6/2018 | Goode |

FOREIGN PATENT DOCUMENTS

| | | |
|---|---|---|
| EP | 1004330 A1 | 5/2000 |
| WO | 199853878 | 12/1998 |
| WO | 9903532 | 1/1999 |
| WO | 9930776 | 6/1999 |
| WO | 0061223 A1 | 10/2000 |
| WO | 0061224 A1 | 10/2000 |
| WO | 2000061223 | 10/2000 |
| WO | 2000061224 | 10/2000 |
| WO | 0238217 A2 | 5/2002 |
| WO | 0243467 A2 | 6/2002 |
| WO | 2002043467 | 6/2002 |
| WO | 02089655 | 11/2002 |
| WO | 2002100481 A1 | 12/2002 |
| WO | 2005051486 A1 | 9/2005 |
| WO | 2007137026 | 11/2007 |
| WO | 2008117296 A1 | 10/2008 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |
| WO | 2015034867 | 3/2015 |
| WO | 2015077425 | 5/2015 |
| WO | 2015077435 | 5/2015 |

OTHER PUBLICATIONS

International Search Report for PCT/US2008/053780, Jun. 8, 2009.
Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.
International Search Report for PCT/US2008/056479, Aug. 20, 2008.
International Search Report for PCT/US2011/027243, Jul. 8, 2011.
Christensen et al., 'Physiologic Specialization at Esophagogastric Junction in Three Species', American Journal of Physiology, vol. 225, No. 6, Dec. 1973, 1265-1270.
Cigaina, Valerio; Long-term Follow-Up of Gastric Stimulation for Obesity: The Mestre 8-Year Experience; Obesity Surgery; 14; 2004; S14-22.
Clarke et al,. 'An Endoscopic Implantable Device Stimulates the LES On-Demand By Remote Control in a Canine Model'; Gastrointestinal Endoscopy, Volum 63, No. 5; 2006, AB103, 759.
Clarke et al., 'An endoscopically implantable device stimulates the lower esophageal sphincter on demand by remote control: a study using a canine model', Endoscopy 2007; 39: 72-76.
Ellis, et al., 'The Prevention of Experimentally Induced Reflux by Electrical Stimulation of the Distal Esophagus', American Journal of Surgery, vol. 115, Apr. 1968, 482-487.
EPO Search Report EP09704463, Jan. 10, 2011, Virender K. Sharma.
European Search Opinion for EP20120779639, Virender K. Sharma, Nov. 25, 2014.
Examination Report for Australian Patent Application No. 2012242533, Oct. 5, 2015.
Examination Report for Australian Patent Application No. 2012250686, Nov. 4, 2015.
Examination Report for New Zealand Patent Application No. 616944, Jun. 17, 2014.
Examination Report for New Zealand Patent Application No. 616944, Nov. 2, 2015.
Extended European Search Report for EPO Application No. 12771852.6, Aug. 28, 2014.
Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.
International Search Report for PCT/US12/053576, Dec. 24, 2012.
International Search Report for PCT/US2007/068907, Aug. 7, 2008.
International Search Report for PCT/US2012/033695, Aug. 7, 2012.
International Search Report for PCT/US2012/036408, Aug. 17, 2012.
International Search Report for PCT/US2013/056520, Apr. 4, 2014.
International Search Report for PCT/US2014/053793, Mar. 27, 2015.
International Search Report for PCT/US2014/066565, Mar. 12, 2015.
International Search Report for PCT/US2014/066578, Mar. 19, 2015.
Jameison, GG et al. "Laparoscopic Nissen Fundoplication". Annals of Surgery, vol. 220. No. 2, p. 139 (1994).
Kahrilas et al., 'Impact of Fundoplication on Bolus Transit Across Esophagogastric Junction', American Physiological Society, 1998, 1386-1393.
Kamath et al., 'Neurocardiac and Cerebral Responses Evoked By Esophageal Vago-Afferent Stimulation in Humans: Effects of Varying Intensities', Cardiovascular Research, 40 (1998) 591-599.
Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, AB79, 222.
Lund et al., 'Electrical Stimulation of Esophageal Smooth Muscle and Effects of Antagonists', American Journal of Physiology, vol. 217, No. 5, Nov. 1969, 1369-1374.
Notice of Allowance dated Apr. 3, 2014 for U.S. Appl. No. 13/447,168.
Notice of Allowance dated Dec. 24, 2014 for U.S. Appl. No. 13/463,803.
Notice of Allowance dated Feb. 20, 2015 for U.S. Appl. No. 14/201,645.
Notice of Allowance dated Jan. 20, 2015 for U.S. Appl. No. 13/602,184.

(56) References Cited

OTHER PUBLICATIONS

Notice of Allowance dated Jan. 20, 2016 for U.S. Appl. No. 14/201,766.
Notice of Allowance dated Jul. 21, 2014 for U.S. Appl. No. 13/447,168.
Notice of Allowance dated Mar. 17, 2014 for U.S. Appl. No. 13/447,168.
Office Action dated Apr. 11, 2014 for U.S. Appl. No. 13/602,184.
Office Action dated Feb. 1, 2016 for U.S. Appl. No. 14/475,736.
Office Action dated Feb. 20, 2015 for U.S. Appl. No. 14/175,927.
Office Action dated Jul. 8, 2014 for U.S. Appl. No. 13/463,803.
Office Action dated Jun. 19, 2015 for U.S. Appl. No. 13/975,162.
Office Action dated Jun. 25, 2015 for U.S. Appl. No. 14/201,766.
Office Action dated Mar. 10, 2016 for U.S. Appl. No. 14/191,085.
Office Action dated Oct. 2, 2015 for U.S. Appl. No. 14/500,856.
Office Action dated Oct. 7, 2015 for U.S. Appl. No. 13/975,162.
Sallam et al., 'Feasibility of gastric electrical stimulation by percutaneous endoscopic transgastric electrodes'; Gastrointestinal Endoscopy; vol. 68, No. 4; 2008, 754-759.
Sanmiguel et al, 'Effect of electrical stimulation of the LES on LES pressure in a canine model'; Am J Physiol Gastrointest Live Physiol; 295: 389-394; 2008.
Shellock, Frank G. 'Rf Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.
Stein et al., 'Three-dimensional Imaging of the Lower Esophageal Sphincter in Gastroesophageal Reflux Disease,' Annual Meeting of the American Surgical Association, Apr. 11-13, 1991, 374-383.
Supplementary European Search Report for EP20120779639, Virender K. Sharma, Nov. 13, 2014.
Tam, WCE et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).
Xing et al., 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.
Xing et al., 'Gastric Electrical Stimulation Significantly Increases Canine Lower Esophageal Sphincter Pressure'; Digestive Diseases and Sciences; vol. 50, No. 8 (Aug. 2005), pp. 1481-1487.
Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.
Office Action dated Jun. 8, 2016 for U.S. Appl. No. 14/475,736.
Office Action dated Mar. 15, 2016 for U.S. Appl. No. 14/695,267.
Office Action dated Mar. 17, 2016 for U.S. Appl. No. 14/500,856.
Office Action dated May 20, 2016 for U.S. Appl. No. 13/975,162.
Office Action dated May 4, 2016 for U.S. Appl. No. 14/548,793.
Notice of Allowance dated Jul. 19, 2016 for U.S. Appl. No. 14/191,085.
Supplementary European Search Report for EP13831668, completed on Apr. 15, 2016.
Office Action dated Aug. 24, 2016 for U.S. Appl. No. 14/753,402.
Office Action dated Aug. 19, 2016 for U.S. Appl. No. 14/943,772.
Notice of Allowance mailed Sep. 27, 2016 for U.S. Appl. No. 14/500,856.
Office Action dated Oct. 3, 2016 for U.S. Appl. No. 14/548,793.
Extended European Search Report for EPO Application No. 16174071.7, Oct. 19, 2016.
International Search Report for PCT/US2015/061108, May 26, 2016.
Notice of Allowance dated Dec. 5, 2016 for U.S. Appl. No. 13/975,162.
Office Action dated Dec. 19, 2016 for U.S. Appl. No. U.S. Appl. No. 14/753,402.
Office Action dated Jan. 18, 2017 for U.S. Appl. No. 14/475,736.
Notice of Allowance dated Feb. 16, 2017 for U.S. Appl. No. 14/943,772.
Notice of Allowance dated Apr. 4, 2017 for U.S. Appl. No. 14/548,793.
Office Action dated Apr. 4, 2017 for U.S. Appl. No. 14/753,402.
Examination Report for EP117514430, dated May 17, 2017.
Supplementary European Search Report for EP14842625, dated Feb. 27, 2017.
Supplementary European Search Report for EP14863570, dated Jun. 30, 2017.
Supplementary European Search Report for EP14864930, dated May 4, 2017.
Notice of Allowance dated Jul. 28, 2017 for U.S. Appl. No. 14/475,736; (pp. 1-8).
Office Action dated Aug. 21, 2017 for U.S. Appl. No. 14/753,402; (pp. 1-9).
Notice of Allowance dated Nov. 8, 2017 for U.S. Appl. No. 14/548,855; (pp. 1-8).
Office Action dated Dec. 20, 2017 for U.S. Appl. No. 14/753,402; (pp. 1-9).
Office Action dated Jan. 26, 2016 for U.S. Appl. No. 14/686,996.
Office Action dated Oct. 17, 2017 for U.S. Appl. No. 14/686,996; (pp. 1-13).
Office Action dated Dec. 21, 2017 for U.S. Appl. No. 15/594, 903.
Examination Report for EP117514430, dated Jan. 17, 2018.
Office Action mailed Aug. 10, 2017 for U.S. Appl. No. 15/170,462; (pp. 1-6).
Office Action mailed Mar. 8, 2018 for U.S. Appl. No. 15/170,462 (pp. 1-5).
Office Action dated Jun. 18, 2015 for U.S. Appl. No. 14/337,006.
Office Action dated Oct. 7, 2015 for U.S. Appl. No. 14/337,006.
Notice of Allowance dated Mar. 2, 2016 for U.S. Appl. No. 14/337,006.
Extended European Search Report for EP17187374.8, Feb. 27, 2018.
First Examination Report for New Zealand Patent Application No. 715619, Jan. 22, 2016.
Office Action dated Feb. 12, 2016 for U.S. Appl. No. 14/665,226.
Office Action dated Jul. 5, 2016 for U.S. Appl. No. 14/665,226.
Notice of Allowance dated Nov. 29, 2016 for U.S. Appl. No. 14/665,226.
Office Action dated May 10, 2018 for U.S. Appl. No. 14/753,402 (pp. 1-9).
Office Action dated Jul. 19, 2018 for U.S. Appl. No. 14/686,996 (pp. 1-17).
Office Action dated Jul. 26, 2018 for U.S. Appl. No. 15/443,983 (pp. 1-5).
Examination Report for EP16174071.7, dated Jul. 26, 2018.
Office Action dated Jun. 29, 2018 for U.S. Appl. No. 15/448,944 (pagese 1-6).
International Search Report for PCT/US2017/062298, Feb. 1, 2018.
International Search Report for PCT/US2019/016923, Jun. 7, 2019.

\* cited by examiner

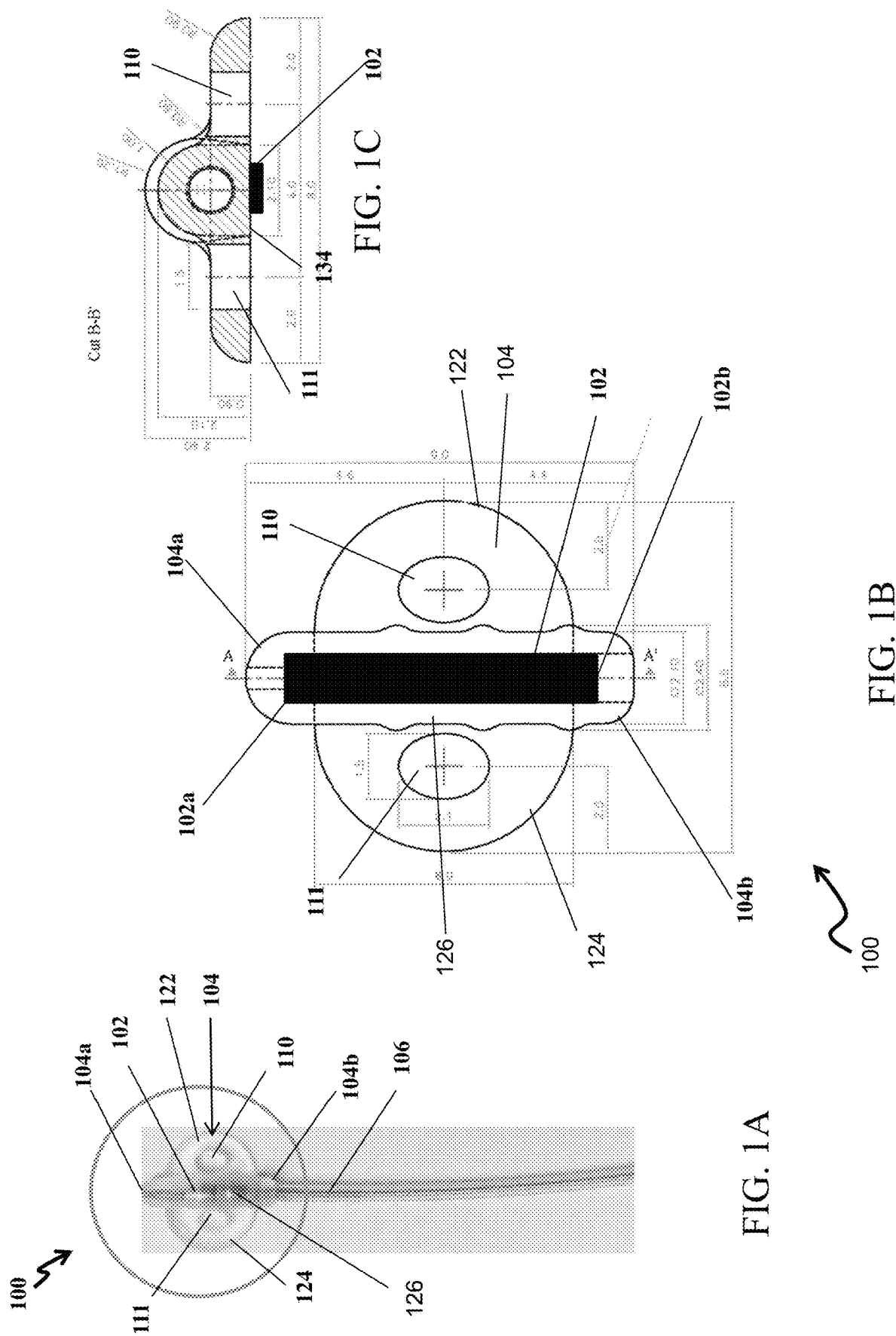

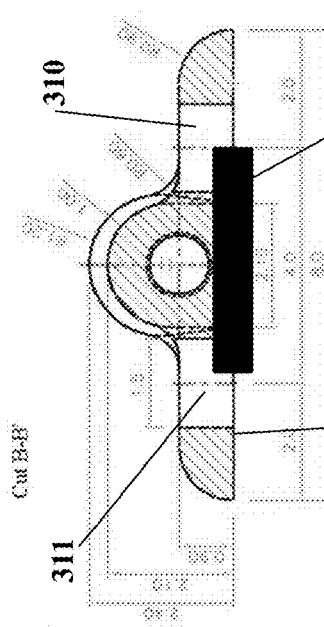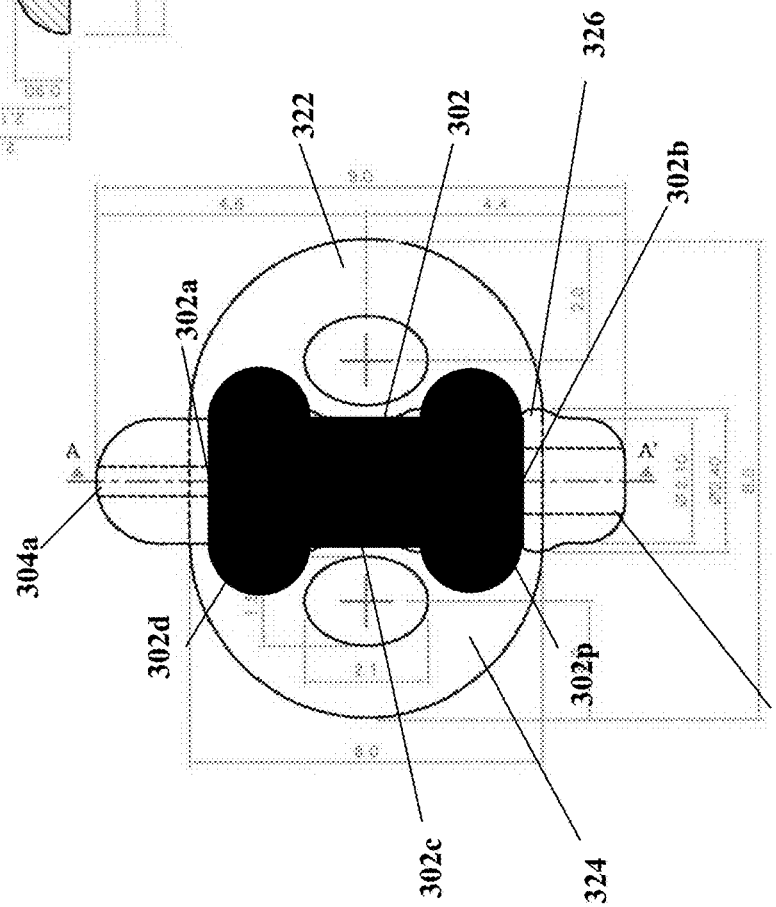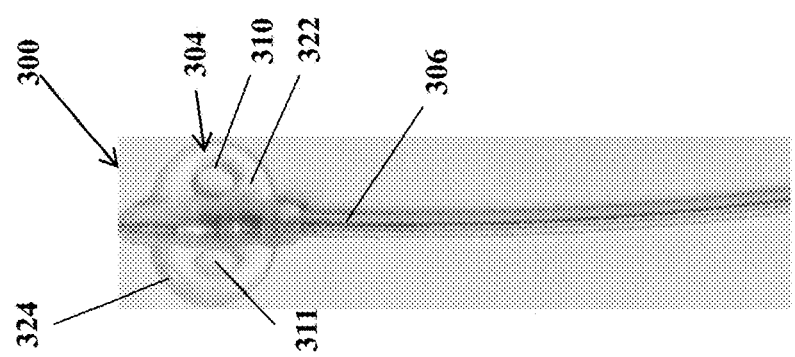

SURFACE ELECTRODES

CROSS-REFERENCE

The present specification relies on U.S. Patent Provisional Application No. 62/482,588 (the "'588 Application"), entitled "Implantable Surface Electrodes and Method of Implantation" and filed on Apr. 6, 2017 for priority. The '588 Application is incorporated herein by reference in its entirety.

FIELD

The present specification relates generally to implantable leads used in the electrical stimulation of human tissues. More particularly, the present specification relates to implantable surface electrodes and corresponding anchors.

BACKGROUND

Electrical stimulation of nerves and surrounding tissue is used to treat a variety of conditions. For example, electrical stimulation can be used to restore partial function to limbs or organs following traumatic injury. Electrical stimulation can also be used to reduce pain and, for purposes of this disclosure, electrical stimulation can be used to treat disorders associated with the gastrointestinal (GI) system, such as gastroesophageal reflux disease (GERD).

Gastro-esophageal reflux disease (GERD) is a common health problem and is expensive to manage in both primary and secondary care settings. This condition results from exposure of esophageal mucosa to gastric acid as the acid refluxes from the stomach into the esophagus. The acid damages the esophageal mucosa resulting in heartburn, ulcers, bleeding, and scarring, and long term complications such as Barrett's esophagus (pre-cancerous esophageal lining) and adeno-cancer of the esophagus.

Electrical stimulation has been employed for use in the treatment of GERD. For example, in U.S. Pat. No. 6,901, 295, assigned to Endostim, Inc., "A method and apparatus for electrical stimulation of the lower esophageal sphincter (LES) is provided. Electrode sets are placed in the esophagus in an arrangement that induce contractions of the LES by electrical stimulation of the surrounding tissue and nerves. The electrical stimulus is applied by a pulse generator for periods of varying duration and varying frequency so as to produce the desired contractions. The treatment may be short-term or may continue throughout the life of the patient in order to achieve the desired therapeutic effect. The stimulating electrode sets can be used either alone or in conjunction with electrodes that sense esophageal peristalsis. The electrode sets can be placed endoscopically, surgically or radiologically." The referenced invention relies on sensing certain physiological changes in the esophagus, such as changes in esophageal pH, to detect acid reflux. Once a change in esophageal pH is recognized, the system generates an electrical stimulation in an attempt to instantaneously close the LES and abort the episode of acid reflux. U.S. Pat. No. 6,901,295 is hereby incorporated by reference in its entirety. In addition, U.S. Pat. Nos. 7,738,961, 9,345,879, 9,561,367, 8,712,529, 9,061,147, 8,712,530, 8,447,403, 8,447,404, 9,381,344, 8,831,729, 9,037,245, 9,498,619, 8,798,753, 8,543,210, 9,623,238, 9,616,225, 9,020,597, 9,724,510, 9,682,234, 8,538,534, 8,160,709, 9,789,309, 9,827,425, and 9,925,367, all assigned to EndoStim, Inc., are all hereby incorporated by reference in their entirety.

The leads used in electrical stimulation of gastrointestinal tissues traditionally comprise elongated or coiled insulated wires or cables having a means for attachment to an electrical pulse generator at one end and one or more exposed electrodes at the other end. The leads are typically anchored in place such that the electrodes are positioned and remain proximate the target nerve or tissues. Anchoring is often accomplished by suturing the electrode containing ends of the leads proximal to the electrodes and into the surrounding tissue. Traditional leads often comprise a needle attached to a length of suture nylon at the distal end of each branch of the lead. In some cases, a butterfly shaped anchoring element is positioned on each branch adjacent to each electrode. The needle and suture nylon are used to create a pathway for the electrode to be inserted into the tissue, with the needle and most of the suture being removed thereafter. The remaining suture is used as a tether onto which at least one clip (e.g., titanium clip) is used to provide a distal stop thus preventing the electrode from backing out until sufficient fibrosis is formed.

United States Patent Application Number 2016/0030734, titled 'Endoscopic Lead Implantation Method', and assigned to Endostim, Inc., discloses an example of a method of implantation of an electrically conductive lead to provide electrical stimulation to target tissues. The '734 application describes a method of implanting electrically conductive leads in the gastrointestinal musculature for stimulating target tissues using an endoscopic approach through the patient's esophagus. An endoscope is inserted into the esophagus of a patient. The mucosal surface of the anterior esophagus is punctured in the region encompassing the lower esophageal sphincter (LES). A tunnel is created through the submucosa and exits at the muscularis propria, adventitia, or serosal side of the stomach. The lead is navigated further to the anterior abdominal wall. A first end of the lead remains within the gastrointestinal musculature while a second end of the lead is positioned just outside the anterior abdominal wall. The first end of the lead comprises at least one electrode. An implantable pulse generator (IPG) is implanted and operably connected to the second end of the lead to provide electrical stimulation to target tissues. U.S. Patent Publication Number 2016/0030734 is hereby incorporated by reference in its entirety.

An example of a butterfly-shaped anchoring mechanism is disclosed in United States Patent Application Number 2015/0297885, titled 'Implantable Electrical Stimulation Leads', and assigned to Endostim, Inc. The '885 application describes implantable electrical stimulation leads for the treatment of biological conditions that include a lead body with an electrical connector at one end and multiple in-line electrodes at the other end. The lead body has a length ranging from 350 mm to 630 mm to allow for implantation from an incision site further removed from the final positioning site of the electrodes. One lead has a suture loop extending from the most distal electrode for pulling the lead through the working channel of an endoscope. Another lead has a length of suture with a free end attached to the most distal electrode. Yet another lead has a length of suture attached to the most distal electrode at one end and a needle at the other end. The needle has a curve designed to facilitate maneuvering in confined anatomy. The lead having the needle is designed to be implanted laparoscopically. U.S. Patent Publication Number 2015/0297885 is hereby incorporated by reference in its entirety.

Electrical stimulation leads known in the prior art typically comprise an anchor and an insulated electrode positioned proximate the anchor. Conventionally, in order to laparoscopically implant a stimulating lead comprising an electrode, for example, in the muscularis of the lower esophageal wall of a patient, a laparoscope is inserted into a patient's abdominal cavity through an incision in the patient's abdominal wall and a portion of an abdominal esophagus is exposed. An electrode, as part of a stimulating lead, is then delivered through a laparoscopic port and advanced to a target position at the muscular layer of the lower esophageal sphincter (LES) wall. Next, a needle and suture attached to the distal end of the lead is used to pass through the LES wall and pull the electrode into the muscular layer of the LES. The electrode is pulled into the LES muscular layer so that the electrode becomes physically embedded within the tissue, wherein the electrode being physically embedded is defined as the electrode being typically positioned such that it is covered by tissue around the entire periphery of its body. Then, using a separate needle and suture, the anchor is sutured to the proximate anatomy to anchor the lead in place.

Conventional lead designs, along with their placement methods requiring electrodes to be stitched into the thin muscle wall of the LES, have a plurality of disadvantages. Conventional lead implantation requires electrodes to be stitched into the thin muscle wall of the LES, which is approximately 2-3 mm thick. This stitching requires an endoscopic check during surgery to ensure that the stitch is not too deep causing the electrode to go through the LES muscle wall and through the mucosal lining. This may lead to migration/erosion of the electrode and lead body into the patient's esophagus. However, an endoscopic check is very cumbersome because it requires endoscopy equipment to be made available in the operating room along with the presence of a doctor for performing the endoscopy procedure. This adds both significant time and cost to the overall procedure. Further, an endoscopic check may provide false negatives, due to the difficulty in determining excessively deep stitching. If the electrode does not penetrate all the way through the mucosal lining, but is just under the skin surface, a false negative may be obtained, leading to erosion of the electrode and lead body in the lumen of the esophagus over time.

There is a need for a new design of the electrical stimulation lead that does not require the electrode to be stitched into the patient's tissue and for a design that would enable implanting an anchor into the patient's tissue without requiring the electrode to be present. There is also need for a method of implantation of the lead that does not require an endoscopic check during surgery to ensure the correct penetration depth and thereby prevent potential migration/erosion of the remaining electrode and lead body into the esophagus. Further, there is need for a lead design and method of implantation that prevents erosion of the electrode and lead body into the lumen of a patient's esophagus or gastrointestinal tissue over time.

SUMMARY

The present specification discloses an implantable electrical stimulation lead, comprising: at least one surface electrode, wherein the at least one surface electrode is configured to be placed on top of a tissue surface in contact with the tissue surface, but not embedded within the tissue surface; and an anchor coupled to and covering the at least one surface electrode.

The at least one surface electrode may be a machined platinum iridium electrode or may comprise alternating platinum iridium coils. The anchor may comprise silicone.

Optionally, the anchor comprises a distal end and a proximal end, and further comprises: two opposing symmetric D-shaped members, each of the two opposing symmetric D-shaped member comprising a straight edge and a curved edge; a central portion attached to the straight edges of each D-shaped member, and having a length greater than the length of the straight edges; and a cylindrical suture sleeve connected to the central portion at the proximal end.

Optionally, each of the two opposing symmetric D-shaped members comprises an aperture. Optionally, the cylindrical suture sleeve comprises a groove configured to receive a suture. The at least one surface electrode may be positioned within the central portion of the anchor. Optionally, the at least one surface electrode is of a length greater than the length of the straight edges of each of the two opposing symmetric D-shaped members, and shorter than the length of the central portion. Optionally, the at least one surface electrode is of a length shorter than the length of the straight edges of each of the two opposing symmetric D-shaped members.

Optionally, the at least one surface electrode has a proximal portion, a distal portion, and a central portion wherein said proximal portion and distal portion each have a width that is greater than a width of the central portion.

Optionally, the anchor comprises a distal end and a proximal end, and further comprises: a parallelogram-shaped structure with two equal, opposite, and parallel longer edges that are adjacent to two equal and opposite shorter edges, wherein the two shorter edges are curved outwards away from the structure, and wherein a first parallel longer edge comprises a proximal edge corresponding to the proximal end and a second parallel longer edge comprises a distal edge corresponding to the distal end, the structure comprising: two symmetrical and opposing side portions with each portion containing one of the two shorter edges; a central portion positioned between the two symmetrical and opposing side portions; and a cylindrical suture sleeve connected to the central portion at the proximal end.

Optionally, the anchor is coupled to and covers two surface electrodes wherein one of the two surface electrodes is positioned in one of the two symmetrical and opposing side portions. Each of the two surface electrodes may be flanked by at least one aperture along a length of each of the two surface electrodes.

Optionally, the longer edges are perpendicular to the shorter edges. Optionally, the longer edges are at angles other than perpendicular to the shorter edges.

The implantable electrical stimulation lead may further comprises a suture and needle at a distal end of the anchor.

The present specification also discloses a method of implanting an electrical stimulation lead comprising a surface electrode, said method comprising: advancing an electrical stimulation lead comprising a surface electrode and an anchor element to a target tissue location; and securing said anchor element to said target tissue location such that said surface electrode is positioned on top of said target tissue location but not embedded within said target tissue location such that at least a portion of an external periphery surface of said surface electrode is not covered by a tissue at said target tissue location.

Optionally, said anchor element comprises at least one aperture and securing said anchor element to said target tissue location comprises passing a suture through said at least one aperture and said target tissue location. Optionally, said anchor element comprises at least one groove and securing said anchor element to said target tissue location comprises passing a suture within said at least one groove and through said target tissue location. Optionally, said anchor element comprises at least one aperture and at least one groove and securing said anchor element to said target tissue location comprises passing a suture through said at least one aperture, within said at least one groove, and through said target tissue location.

Optionally, said electrical stimulation lead further comprises a distal suture and needle and said method further comprises securing said distal suture to a patient's anatomy to maintain the lead in place and then removing said distal suture after said anchor element is secured to said target tissue location.

The present specification also discloses an implantable electrical stimulation lead, comprising: at least one surface electrode, wherein the at least one surface electrode is placed on a tissue surface in contact with the tissue surface; an anchor coupled to and covering the surface electrode, the anchor comprising a proximal end and a distal end; and a cylindrical suture sleeve connected to the proximal end of the anchor.

Optionally, the cylindrical suture sleeve comprises a groove at a center of a length of the cylindrical suture sleeve, wherein the cylindrical suture sleeve has a first diameter at the center of its length on either side of the groove, wherein the diameter of the cylindrical suture sleeve at the center changes gradually to a second diameter towards either end of the cylindrical suture sleeve, and wherein the first diameter is greater than the second diameter.

Optionally, the implantable electrical stimulation lead further comprises a suture and needle at a distal end of said anchoring mechanism.

The present specification also discloses an implantable electrical stimulation lead, comprising: at least one surface electrode, wherein the at least one surface electrode is configured to be placed on top of a tissue surface, wherein the at least one surface electrode comprises: a central portion having a first width; a distal portion having a second width; and a proximal portion having a third width, wherein the second width of the distal portion and the third width of the proximal portion are each greater than the first width of the central portion; and an anchor coupled to and covering said portions of the at least one surface electrode, along a longitudinal axis of said portions.

Optionally, a lower surface of the central cylindrical portion of the at least one surface electrode is flat.

Optionally, the two cylindrical portions on either ends of the central cylindrical portion each comprise a cylindrical cavity of a third radius, wherein the second radius is greater than the third radius.

Optionally, a distal end of one of the two cylindrical portions which is proximal to a distal end of the surface electrode comprises a hole.

Optionally, the implantable electrical stimulation lead further comprises a suture and needle at a distal end of the anchor.

The present specification also discloses an implantable electrical stimulation lead, comprising: at least one surface electrode, wherein the at least one surface electrode is placed on a tissue surface in contact with the tissue surface and an anchoring mechanism coupled to and covering the surface electrode.

The electrode may be a machined platinum iridium electrode. Alternatively, the electrode may comprise alternating platinum iridium coils. The anchoring mechanism may be manufactured using silicone.

The anchoring mechanism includes a distal end and a proximal end, and optionally comprises: two symmetrically opposing D-shaped members, each member comprising a straight edge and a curved edge; a central portion combined to the straight edges of each D-shaped member, and having a length greater than the length of the straight edges; and a cylindrical suture sleeve connected to the central portion at the proximal end.

Each opposing D-shaped member may comprise an aperture. The cylindrical suture sleeve may comprise a groove in which a suture is placed. The at least one surface electrode may be placed along a surface of the central portion of the anchoring mechanism. Optionally, the at least one surface electrode is of a length greater than the length of the straight edges of each D-shaped member, and shorter than the length of the central portion. Optionally, the at least one surface electrode is of a length shorter than the length of the straight edges of each D-shaped member.

Optionally, a width of the at least one surface electrode is different at different lengths of the surface electrode.

The anchoring mechanism includes a distal end and a proximal end, and optionally comprises: a parallelogram-shaped structure with two equal, opposite, and parallel longer edges that are adjacent to two equal and opposite shorter edges, wherein the two shorter edges are curved outwards away from the structure, and wherein each parallel longer edge includes a proximal edge corresponding to the proximal end and a distal edge corresponding to the distal end, the structure comprising: two symmetrical and opposing side portions with each portion containing one of the two shorter edges; a central portion central to and combined with the side portions; and a cylindrical suture sleeve connected to the central portion at the proximal end.

Optionally, the anchoring mechanism is coupled to and covers two surface electrodes, one surface electrode positioned in each of the two symmetrical and opposing side portions. Each surface electrode may be flanked by at least one aperture on either side along a length of each surface electrode.

The longer edges may be perpendicular to the shorter edges and may be at angles other than perpendicular to the shorter edges.

The present specification also discloses an implantable electrical stimulation lead, comprising: at least one surface electrode, wherein the at least one surface electrode is placed on a tissue surface in contact with the tissue surface; an anchor coupled to and covering the surface electrode, the anchor comprising a proximal end and a distal end; and a cylindrical suture sleeve connected to the proximal end of the anchor.

Optionally, the cylindrical suture sleeve comprises a groove at the center of a length of the cylindrical suture sleeve; wherein the cylindrical suture sleeve has a first diameter at the center of its length on either side of the groove, wherein the diameter of the cylindrical suture sleeve at the center changes gradually to a second diameter towards either end of the cylindrical suture sleeve, wherein the first diameter is greater than the second diameter.

The present specification also discloses an implantable electrical stimulation lead, comprising: at least one surface electrode, wherein the at least one surface electrode is placed on a tissue surface in contact with the tissue surface; the surface electrode comprising: a central cylindrical portion with a first radius; two cylindrical portions of a second radius on both ends of the central cylindrical portion, wherein the first radius is greater than the second radius; and an anchor coupled to and covering a portion of the cylindrical portions of the surface electrode, along the longitudinal axis of the cylindrical portions.

Optionally, the two cylindrical portions on both ends of the central cylindrical portion each comprise a cylindrical cavity of a third radius, wherein the second radius is greater than the third radius.

Optionally, a distal end of one of the two cylindrical portions which is proximal to a distal end of the surface electrode comprises a hole.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 1A illustrates a design of an implantable electrical stimulation lead, in accordance with an embodiment of the present specification;

FIG. 1B illustrates a close up view of the implantable electrical stimulation lead shown in FIG. 1A;

FIG. 1C illustrates a sectional view of the implantable electrical stimulation lead shown in FIG. 1A;

FIG. 3A illustrates a design of an implantable electrical stimulation lead, in accordance with another embodiment of the present specification;

FIG. 3B illustrates a close up view of the implantable electrical stimulation lead shown in FIG. 3A;

FIG. 3C illustrates a sectional view of the implantable electrical stimulation lead shown in FIG. 3A.

DETAILED DESCRIPTION

Figures 2A, 2B:
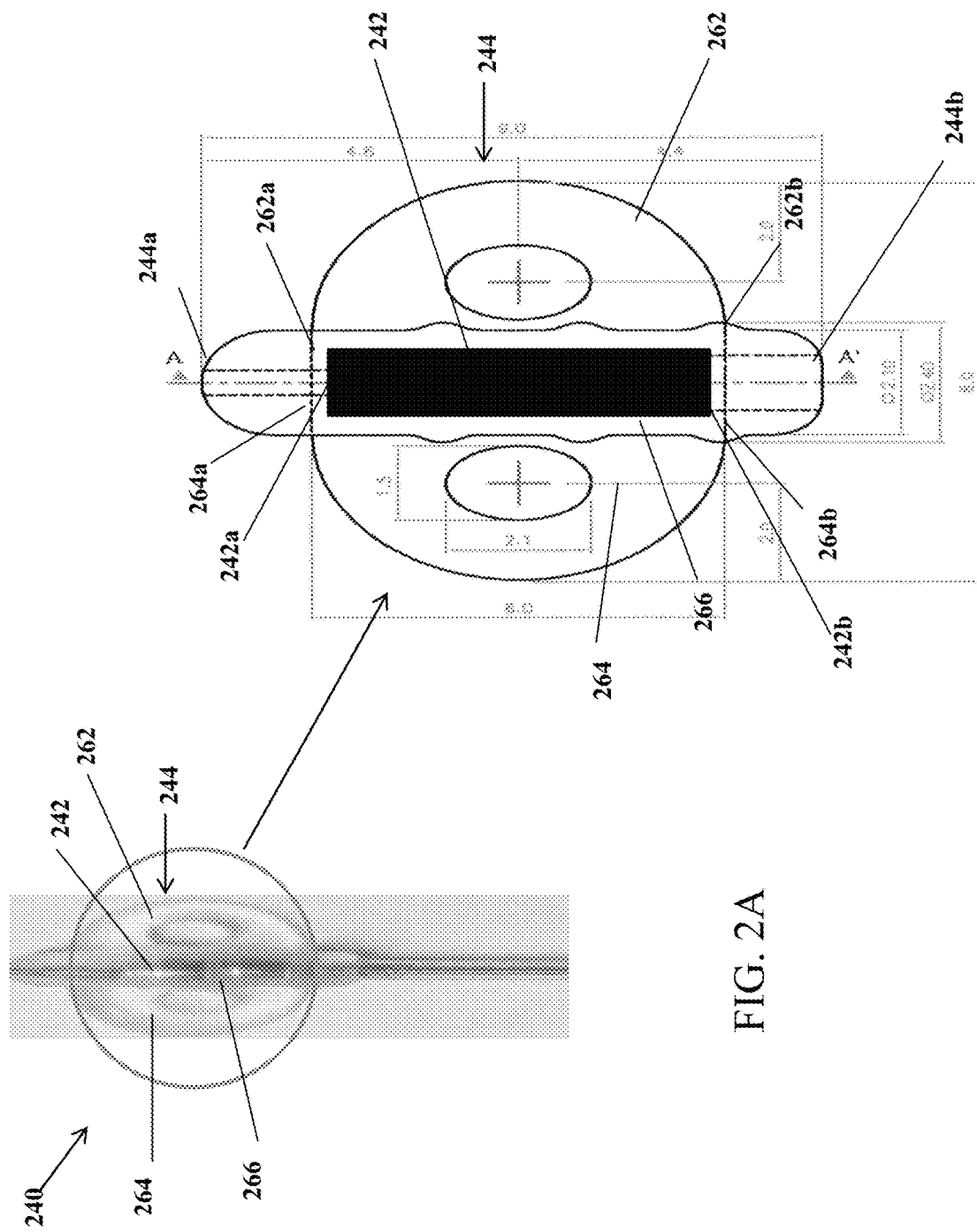
FIG. 2A illustrates a design of the implantable electrical stimulation lead wherein the electrode is completely covered by the anchor, in accordance with an embodiment of the present specification.
FIG. 2B illustrates a close up view of the implantable electrical stimulation lead shown in FIG. 2A.

The present specification discloses an implantable electrical stimulation lead that is dimensioned specifically for use in confined anatomy, particularly the area proximate the gastroesophageal junction (GEJ). The lead is designed to be implanted laparoscopically and comprises an implantable surface electrode and an anchoring member that covers the electrode when placed at an implant site. The electrode provided by the present specification does not require to be buried or physically embedded into tissue, but can rest on the surface while being coupled and covered by an anchoring element. In embodiments of the present specification, the electrode is positioned such that at least a portion of the external periphery surface of the electrode is not covered by tissue. In embodiments, at least a portion of the anchor of the stimulation lead covers at least a portion of the electrode. In embodiments, the dimensions and relative sizing of the anchor of the stimulation leads is critical to achieving a combination of goals including: contributing to the ease of attachment of the lead to a tissue; contributing to the ease of delivery of the lead to an implantation site; and possessing the ability to securely hold and position an electrode, of the required size, in the desired position. In some embodiments, the electrode is a machined platinum iridium electrode. In other embodiments, the electrode comprises alternating platinum iridium coils. In some embodiments, the anchoring mechanism is manufactured using silicone. The present specification also discloses a method of laparoscopically implanting the stimulating lead comprising the surface electrode in the muscular layer of a lower esophageal wall of a patient.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

In various embodiments of the present specification, the implantable electrical stimulation lead device is configured such that the electrode used for providing electrical stimulation to a tissue region is not embedded in, and does not pierce through, the tissue, but is placed on a surface of the tissue, in contact with the tissue. Therefore, the implantable electrical stimulation device is a surface electrode. A first side of the surface electrode is placed on the tissue surface, while a second and opposite side to the first side, is attached to an anchoring member. In embodiments, the anchoring member comprises a winged, spread-out region, and a cylindrical suture sleeve. In various embodiments, the anchoring member comprises a butterfly tab. The lower esophageal sphincter (LES) muscle wall is thin enough such that the stimulation effect caused by the electric field of the lead is strong enough to capture the same neuromuscular tissue as is accomplished by a stitched electrode.

FIG. 1A illustrates a design of an implantable electrical stimulation lead 100, in accordance with an embodiment of the present specification. FIG. 1B illustrates a close up view of an encircled portion of implantable electrical stimulation lead 100 shown in FIG. 1A. FIG. 1C illustrates a sectional view of implantable electrical stimulation lead 100 shown in FIG. 1A.

Referring simultaneously to FIGS. 1A, 1B, and 1C, implantable electrical stimulation lead 100 comprises an electrode 102 having a distal end 102a and a proximal end 102b. In embodiments, electrode 102 is attached to an anchor 104. In various embodiments, anchor 104 comprises a butterfly tab. Anchor 104 may include two opposing D-shaped members (or winged portions) 122 and 124, which align with each other along their vertical and straight edge, while the other two curved, semi-circular edges of winged portions 122 and 124 are pointed away from the central portion 126 where the straight edges merge. Anchor 104 enables anchoring of implantable electrical stimulation lead 100 inside the body of a patient, at the required location, such as on an outer surface of the LES muscle wall without having to individually or separately attach the electrode to tissue. In embodiments, anchor 104 comprises a distal end 104a, and a proximal end 104b. Distal end 104a and proximal end 104b may be located at the meeting of the curved edges of portions 122 and 124 of anchor 104 with a central portion 126 of anchor 104. Proximal end 104a of anchor 104 is coupled with a proximal suture sleeve 106. Suture sleeve 106 may comprise a groove (not shown) in which a suture can be placed for attaching anchor 104 with the patient's tissue.

In embodiments, electrode 102 is placed along central portion 126 of anchor 104, where the straight edges of the two D-shaped sides 122 and 124 of anchor 104 merge with each other. Electrode 102 is placed along the longitudinal axis of central portion 126 of anchor 104. In embodiments, as shown in FIG. 1C, electrode 102 is situated on a lower surface 134 of anchor 104 that faces the patient's tissue, where the electrical stimulation may be required for treatment of the patient. Because the electrode is positioned between the tissue and the anchor, which is physically attached to the tissue, the electrode itself need not be physically connected to the tissue. In an embodiment, and as shown in FIG. 1B, a portion of distal end 102a of electrode 102 placed on a lower surface 134 of anchor 104, protrudes beyond a distal end of the winged portions 122, 124 but is positioned within the central portion 126 at the distal end 104a of the anchor 104. Similarly, in an embodiment, a portion of proximal end 102b of electrode 102 protrudes beyond a proximal end of the winged portions 122, 124 but is positioned within the central portion 126 at the proximal end 104b of the anchor 104.

Referring to FIG. 1B, in embodiments, anchor 104 comprises first winged portion 122, second winged portion 124, and central portion 126. Vertical edges of winged portions 122 and 124 merge with each other within central portion 126. In some embodiments, central portion 126 is an elongated cylindrical structure having a length ranging from approximately 5 mm to 15 mm, with curved (dome-shaped) edges at its ends. In an embodiment, central portion 126 has a length of approximately 9 mm. In an embodiment, an upper surface of central portion 126, along its longitudinal axis, is shaped like a cylinder, of approximately 9 mm in length. In some embodiments, central potion 126 has a diameter ranging from approximately 1 mm to 5 mm. In embodiments, central portion 126 has a length greater than the length of the vertical edges of winged portions 122 and 124. In some embodiments, vertical edges of winged portions 122 and 124 range from approximately 4 mm to 11 mm in length, where they merge with central portion 126. In an embodiment, vertical edges of winged portions 122 and 124 are approximately 6 mm in length, where they merge with central portion 126. In some embodiments, each of winged portions 122, 124 extend outward from central portion 126 a distance, or have a width, ranging from approximately 2 mm to 5 mm. Lower surface 134, opposite the upper surface, of central portion 126 may include a level surface where electrode 102 is attached. The upper cylindrical surface of central portion 126 may have a diameter of 2.10 mm. At certain intervals, the cylindrical surface of central portion 126 may have a larger diameter, ranging from 2.10 mm to 2.70 mm, or of approximately 2.4 mm, resulting in curves or bumps over its cylindrical surface. In some embodiments, a total width of anchor 104, extending from a farthest point (from the longitudinal axis of central portion 126) on the curved edge of one winged portion (122) to another farthest point (from the longitudinal axis of central portion 126) on the curved edge of second winged portion (124), ranges from approximately 5 mm to 15 mm and, in one embodiment, is approximately 8 mm.

The left edge of first winged portion 122 is attached to, and extends a portion of the length of, central portion 126 and, therefore, has a length that is less than the length of the central portion 126 and is, in an embodiment, approximately 6 mm. From central portion 126, first winged portion 122 extends to the right in a semi-circular shape. The semi-circular shape may have a radius in a range of 2 mm to 5 mm and, in one embodiment, of approximately 4 mm. Located in the middle of first winged portion 122 is a first aperture 110. In an embodiment, a center of the first aperture 110 is positioned approximately 2.0 mm from the furthest right or outer edge of first winged portion 122, approximately 4.6 mm from the distal edge of central portion 126, and approximately 4.4 mm from the proximal edge of central portion 126. In embodiments, the first aperture 110 has an oval shape with a first axis parallel to the longitudinal axis of central portion 106 of approximately 2.1 mm, and second axis perpendicular to the first axis of a length that approximates 1.5 mm. In other embodiments, first aperture 110 is positioned in different locations within winged portion 122, such as further proximally or distally, or further toward the outer edge of winged portion 122 or toward central portion 126, and has a circular shape or oval shape with a first longitudinal axis that is less than a second perpendicular axis.

In embodiments, second winged portion 124 is substantially similar to first winged portion 122, except that it is placed on the opposite (left) side of central portion 126 in a symmetrical relationship to first winged portion 122. The right edge of second winged portion 124 merges with, and extends a portion of the length of, central portion 126 and, therefore, has a length that is less than the length of the central portion 126 and, in an embodiment, approximates 6 mm. From central portion 126, second winged portion 124 extends to the left in a semi-circular shape. The semi-circular shape may have a radius in a range of 2 mm to 5 mm and, in one embodiment, of approximately 4 mm. Located in the middle of second winged portion 124 is a second aperture 111. In an embodiment, a center of the second aperture 111 is positioned approximately 2.0 mm from the furthest left or outer edge of second winged portion 124, approximately 4.6 mm from the distal edge of central portion 126, and approximately 4.4 mm from the proximal edge of central portion 126. In embodiments, the second aperture 111 has an oval shape with a first axis parallel to the longitudinal axis of central portion 126 of approximately 2.1 mm, and second axis perpendicular to the first axis of a length that approximates 1.5 mm. In other embodiments, second aperture 111 is positioned in different locations within winged portion 124, such as further proximally or distally, or further toward the outer edge of winged portion 124 or toward central portion 126, and has a circular shape or oval shape with a first longitudinal axis that is less than a second perpendicular axis.

In embodiments, first and second winged portions have a thickness in a range of approximately 0.3 to 1.5 mm and, in one embodiment, of approximately 0.9 mm. The curved edges of portions 122 and 124 may transition from the upper surface of anchor 104 to its lower surface in a smooth, curved manner. Referring to FIG. 1C, in an embodiment, the quadrant formed between the outer curved edges of portions 122 and 124 and the nearest edge of their respective apertures, have a radius of approximately 0.9 mm. In some embodiments, an optional distal suture with needle is included and used to hold the anchor in place as the surgeon secures it in place using apertures 110, 111.

FIG. 1B illustrates an embodiment of an electrode 102 that has a length longer than the length of winged portions 122 and 124, and shorter than the length of central portion 126.

FIGS. 2A and 2B illustrate a design of an implantable electrical stimulation lead 240 in accordance with another embodiment of the present specification. In this embodiment, a length of electrode 242 is shorter than the length of winged portions 262 and 264, and therefore is placed within central portion 266 as well as within the lengths of winged portions 262 and 264.

FIG. 2B illustrates a dimensional view of the implantable electrical stimulation lead 240 shown in FIG. 2A. As seen in the figure, distal and proximal ends 242a, 242b of electrode 242 do not extend beyond distal end 244a and proximal end 244b of anchor 244, respectively, or beyond distal ends 262a, 264a and proximal ends 262b, 264b of winged portions 262, 264. Optionally, in another embodiment, the length of electrode 242 is the same as the length of electrode 102 shown in FIG. 1B but the anchor 244, including the central portion 266 and the winged portions 262, 264 has a length greater than the respective anchor portions of FIG. 1B, such that the ends of electrode 242 do not extend beyond the central portion 266 or winged portions 262, 264 of anchor 244.

FIG. 3A illustrates a design of an implantable electrical stimulation lead, in accordance with yet another embodiment of the present specification. FIG. 3B illustrates a close up view of the implantable electrical stimulation lead shown in FIG. 3A. FIG. 3C illustrates a sectional view of the implantable electrical stimulation lead shown in FIG. 3A. Referring simultaneously to FIGS. 3A, 3B and 3C, an implantable electrical stimulation lead 300 comprises an electrode 302 having a rounded distal end 302a and a rounded proximal end 302b. The rounded distal end 302a and proximal end 302b give the electrode 302 a dumbbell shape, increasing the surface area of the electrode-tissue interface, thereby increasing stimulation efficiency.

In embodiments, electrode 302 is attached to an anchor 304. In various embodiment, the electrode 302 comprises a central portion 302c, a distal portion 302d, and a proximal portion 302p. In some embodiments, the central portion 302c has a length ranging from approximately 2 mm to 4 mm and a thickness ranging from approximately 1 mm to 2.2 mm. In some embodiments, the distal end portion 302d and proximal end portion 302p each have a width ranging from approximately 1.5 mm to 5 mm and a thickness ranging from approximately 1 mm to 2 mm. In various embodiments, anchor 304 comprises a butterfly tab. Anchor 304 may include two opposing D-shaped members (or winged portions) 322 and 324, which align with each other along their vertical and straight edge, while the other two curved, semi-circular edges of winged portions 322 and 324 are pointed away from the central portion where the straight edges merge. Anchor 304 enables anchoring of implantable electrical stimulation lead 300 inside the body of a patient, at the required location, such as on an outer surface of the LES muscle wall. In embodiments, anchor 304 comprises a distal end 304a and a proximal end 304b. Distal and proximal ends 304a and 304b may be located at the points where straight edges of winged portions 322 and 324 meet a central portion 326 of anchor 304. Central portion 326 is the portion between winged portions 322 and 324, where the straight edges of winged portions 322 and 324 merge with each other. Proximal end 304a of anchor 304 is coupled with a proximal suture sleeve 306. Suture sleeve 306 may comprise a groove (not shown) in which a suture can be placed for attaching anchor 304 with the patient's tissue.

In embodiments, electrode 302 is placed along central portion 326 of anchor 304, where the straight edges of the two D-shaped sides 322 and 324 of anchor 304 merge with each other. Electrode 302 is placed along the longitudinal axis of the central portion 326 of anchor 304. In embodiments, electrode 302 is situated on a lower surface 334 of anchor 304 that faces the patient's tissue where the electrical stimulation may be required for treatment of the patient. In an embodiment, and as shown in FIG. 3B, length of electrode 302 extending from distal end 302a to proximal end 302b, is shorter than the length between ends 304a and 304b of anchor 304.

Referring to FIG. 3B, in embodiments, anchor 304 comprises first winged portion 322, second winged portion 324, and central portion 326. In various embodiments, the dimensional ranges of anchor 304 are the same as or similar to those of anchor 104 of FIGS. 1A-1C. Vertical edges of winged portions 322 and 324 merge with each other within central portion 326. In some embodiments, central portion 326 is an elongated cylindrical structure having a length ranging from approximately 5 mm to 15 mm, with curved (dome-shaped) edges at its ends. In an embodiment, central portion 326 is an elongated cylindrical structure having a length of approximately 9 mm, with curved (dome-shaped) edges at its ends. In an embodiment, an upper surface of central portion 326, along its longitudinal axis, is shaped like a cylinder, of approximately 9 mm in length. In some embodiments, central potion 326 has a diameter ranging from approximately 1 mm to 5 mm. In embodiments, central portion 326 has a length greater than the length of the vertical edges of winged portions 322 and 324. In some embodiments, vertical edges of winged portions 322 and 324 range from approximately 4 mm to 11 mm in length, where they merge with central portion 326. In an embodiment, vertical edges of winged portions 322 and 324 are approximately 6 mm in length, where they merge with central portion 326. In some embodiments, each of winged portions 322, 324 extend outward from central portion 326 a distance, or have a width, ranging from approximately 2 mm to 5 mm. Lower surface 334, opposite the upper surface, of central portion 326 may include a level/planar surface where electrode 302 is attached. The upper cylindrical surface of central portion 326 may have a diameter of 2.10 mm. At certain intervals, the cylindrical surface of central portion 326 may have a larger diameter, ranging from 2.10 mm to 2.70 mm, or of approximately 2.4 mm, resulting in curves or bumps over its cylindrical surface. In some embodiments, a total width of anchor 304, extending from a farthest point (from the longitudinal axis of central portion 326) on the curved edge of one winged portion (322) to another farthest point (from the longitudinal axis of central portion 326) on the curved edge of second winged portion (324), ranges from approximately 5 mm to 15 mm and, in one embodiment, is approximately 8 mm.

The left edge of first winged portion 322 is attached to, and extends a portion of the length of, central portion 326 and, therefore, has a length that is less than the length of the central portion 326 and is, in an embodiment, approximately 6 mm. From central portion 326, first winged portion 322 extends to the right in a semi-circular shape. The semi-circular shape may have a radius in a range of 2 mm to 5 mm and, in one embodiment, of approximately 4 mm. Located in the middle of first winged portion 322 is a first aperture 310. In an embodiment, a center of the first aperture 310 is positioned approximately 2.0 mm from the furthest right or outer edge of first winged portion 322, approximately 4.6 mm from a distal edge of central portion 326, and approximately 4.4 mm from a proximal edge of central portion 326. In embodiments, the first aperture 310 has an oval shape with a first axis parallel to the longitudinal axis of central portion 326 of approximately 2.1 mm, and second axis perpendicular to the first axis of a length that approximates 1.5 mm. In other embodiments, first aperture 310 is positioned in different locations within winged portion 322, such as further proximally or distally, or further toward the outer edge of winged portion 322 or toward central portion 326, and has a circular shape or oval shape with a first longitudinal axis that is less than a second perpendicular axis.

In embodiments, second winged portion 324 is substantially similar to first winged portion 322, except that it is placed on the opposite (left) side of central portion 326 in a symmetrical relationship to first winged portion 322. The right edge of second winged portion 324 merges with, and extends a portion of the length of, central portion 326 and, therefore, has a length that is less than the length of the central portion 326 and, in an embodiment, approximates 6 mm. From central portion 326, second winged portion 324 extends to the left in a semi-circular shape. The semi-circular shape may have a radius in a range of 2 mm to 5 mm and, in one embodiment, of approximately 4 mm. Located in the middle of second winged portion 324 is a second aperture 311. A center of the second aperture 311 is positioned approximately 2.0 mm from the furthest left or outer edge of second winged portion 324, approximately 4.6 mm from the distal edge of central portion 326, and approximately 4.4 mm from the proximal edge of central portion 326. In embodiments, the second aperture 311 has an oval shape with a first axis parallel to the longitudinal axis of central portion 326 of approximately 2.1 mm, and second axis perpendicular to the first axis of a length that approximates 1.5 mm. In other embodiments, second aperture 311 is positioned in different locations within winged portion 324, such as further proximally or distally, or further toward the outer edge of winged portion 324 or toward central portion 326, and has a circular shape or oval shape with a first longitudinal axis that is less than a second perpendicular axis. Each aperture allows attaching anchor 304 with patient's tissue by means of a suture.

In embodiments, first and second winged portions have a thickness in a range of approximately 0.3 to 1.5 mm and, in one embodiment, of approximately 0.9 mm. The curved edges of portions 322 and 324 may transition from the upper surface of anchor 304 to its lower surface in a smooth, curved manner. Referring to FIG. 3C, in an embodiment, the quadrant formed between the outer curved edges of portions 322 and 324 and the nearest edge of their respective apertures, have a radius of approximately 0.9 mm. In some embodiments, an optional distal suture with needle is included and used to hold the anchor in place as the surgeon secures it in place using apertures 310, 311.

FIGS. 3B and 3C illustrate an embodiment of electrode 302 that has a length shorter than the length of winged portions 322 and 324, and is positioned centrally on central portion 326. Additionally, in an embodiment and as illustrated in FIG. 3B, electrode 302 is dumbbell or I-shaped, such that its distal end 302a and proximal end 302b are broader than the length extending between the distal ends 302a and 302b. Therefore, electrode 302 comprises three portions extending sequentially from the distal end 302a to the proximal end 302b, and respectively including a distal portion 302d at the distal end 302a, a central portion 302c that connects distal and proximal portions 302d and 302p, and a proximal portion 302p that is substantially symmetrically opposite to distal end 302a and is at the proximal end 302b. In embodiments, length of portions 302d and 302p, extending respectively from the distal and proximal ends towards central portion 302c is approximately 0.9 mm. In embodiments, central portion 302c has a first width, distal portion 302d has a second width, and proximal portion 302p has a third width wherein second and third widths are greater than the first width. Greater width of electrode 302 enables greater coverage of surface area over the body tissue of a patient.

Figures 4A, 4B:
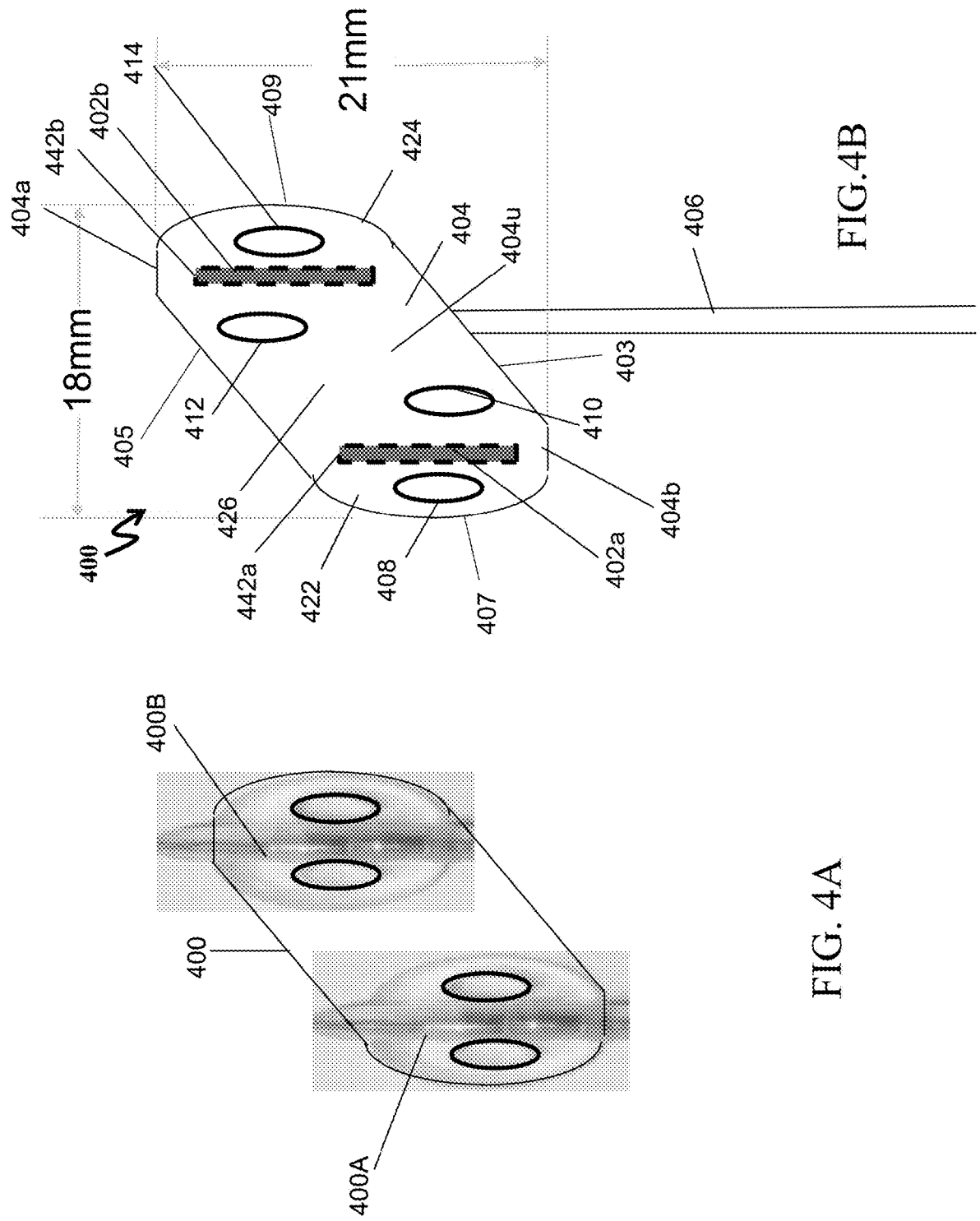
FIG. 4A illustrates a design of an anchor used to cover two surface electrodes in an electrical stimulation lead, in accordance with an embodiment of the present specification.
FIG. 4B illustrates another view of the anchor design shown in FIG. 4A.

In an embodiment where two electrodes are required to be implanted in a patient's body, instead of using two anchors as shown in FIGS. 1A, 2A or 3A above, a single larger anchor may be used. FIG. 4A illustrates a design of an anchor that may be derived from two separate anchors comprising two surface electrodes in an electrical stimulation lead, in accordance with an embodiment of the present specification. FIG. 4B illustrates another view of the anchor design shown derived in FIG. 4A.

Referring to FIG. 4A, a first electrical stimulation lead arrangement 400A and a second electrical stimulation lead arrangement 400B are shown. Design of a third electrical stimulation lead arrangement 400 may be derived from a combination of arrangements 400A and 400B. In some embodiments, each of arrangements 400A and 400B has dimensions the same as or similar to the dimensions of the anchor and electrode shown in FIGS. 1A-1C.

Referring to FIG. 4B, a design of electrical stimulation lead arrangement 400 is illustrated, in accordance with an exemplary embodiment of the present specification. Arrangement 400 includes a single anchor 404 that is shaped like a parallelogram with two opposite and parallel longer edges—a distal longer edge 405 and a proximal longer edge 403, which may or may not be perpendicular to two opposite and parallel shorter edges 407, 409. A first parallel longer edge 403 comprises a proximal edge corresponding to the proximal end of the anchor 404 and a second parallel longer edge 405 comprises a distal edge corresponding to the distal end of the anchor 404. In an embodiment, the two shorter edges curve outwards away from main body of anchor 404, such as the edges of a semi-circle. In an embodiment, the shorter edges are perpendicular to the longer edges. In another embodiment, the shorter edges are not perpendicular to the longer edges. Therefore, each of the two shorter edges is at an acute angle with the first longer edge and at an obtuse angle with the second (opposite) longer edge. In some embodiments, a width of anchor 404, measured from a first short edge to an opposite second short edge, is in a range of approximately 13 mm to 23 mm. In an embodiment, a width of the anchor 404 measured between the two parallel shorter edges is approximately 18 mm. In embodiments, anchor 404 includes two electrodes 402a and 402b, which are positioned longitudinally on either side of a central axis, parallel to the two shorter edges.

Anchor 404 enables anchoring of implantable electrical stimulation lead 400 inside the body of a patient, at the required location, such as on an outer surface of the LES muscle wall. In embodiments, anchor 404 comprises a distal end 404a and a proximal end 404b. In embodiments, a length of the anchor 404 measured as the distance between distal and proximal ends 404a and 404b ranges from approximately 16 mm to 26 mm and, in one embodiment, is approximately 21 mm. In the embodiment where the shorter edges are perpendicular to the longer edges, the distal end is the entire length of distal longer edge, and the proximal end is the entire length of the proximal longer end. Proximal longer edge of anchor 404 is coupled with a proximal suture sleeve 406. In embodiments, proximal suture sleeve 406 is connected at a center of proximal longer edge of anchor 404. Suture sleeve 406 may comprise a groove (not shown) in which a suture can be placed for attaching anchor 404 with the patient's tissue.

In embodiments, anchor 404 comprises a first winged portion 422, a second winged portion 424, and a central portion 426. First and second winged portions 422 and 424 are positioned on either sides of central portion 426. In an embodiment, first winged portion comprises first electrode 402a and second winged portion comprises second electrode 402b. Winged portions 422 and 424 merge with each other within central portion 426.

In an embodiment, an upper surface 404u of anchor 404 incorporates two elongated cylindrical structures 442a, 442b, with curved (dome-shaped) edges at its ends. The upper surface 404u is the surface that is positioned on the opposite side of the surface that is eventually in contact with the body tissue of the patient, where electrical stimulation is required. Each elongated cylindrical structure 442a, 442b may be aligned with, house, and cover an outer surface of one of electrodes 402a and 402b. In an embodiment, cylindrical structures 442a, 442b are positioned within winged portions 422 and 424, and are shaped like cylinders of approximately 9 mm in length.

Lower surface, opposite the upper surface of anchor 404, may include a level/planar surfaces where electrodes 402a and 402b are attached. Each cylindrical structure 442a, 442b in winged portions 422 and 424 may have a diameter of 2.10 mm.

Located on an outer side, facing the nearest shorter edge, of first electrode 402a, in first winged portion 422, is a first aperture 408. A second aperture 410 is located on the other side of electrode 402a, within first winged portion 422. Similarly, on an outer side of second electrode 402b, in second winged portion 424, is a third aperture 414. A fourth aperture 412 is located on the other side of electrode 402b, within second winged portion 424. In embodiments, all apertures 408, 410, 412, and 414 have oval shapes with a first axis parallel to electrodes 402a and 402b, of approximately 2.1 mm, and second axis perpendicular to the first axis of a length that approximates 1.5 mm. In other embodiments, apertures 408, 410, 412, and 414 are circular in shape or oval in shape with first axis parallel to electrodes 402a and 402b that has a length less than a length of a second perpendicular axis. Each aperture allows attaching anchor 404 with patient's tissue by means of a suture.

In embodiments, first and second winged portions 422, 424 have a thickness in a range of approximately 0.3 to 1.5 mm and, in one embodiment, of approximately 0.9 mm. The curved edges of portions 422 and 424 may transition from the upper surface of anchor 404 to its lower surface in a smooth, curved manner. In some embodiments, an optional distal suture with needle is included and used to hold the anchor in place as the surgeon secures it in place using apertures 408, 410, 412, 414.

Figure 5:
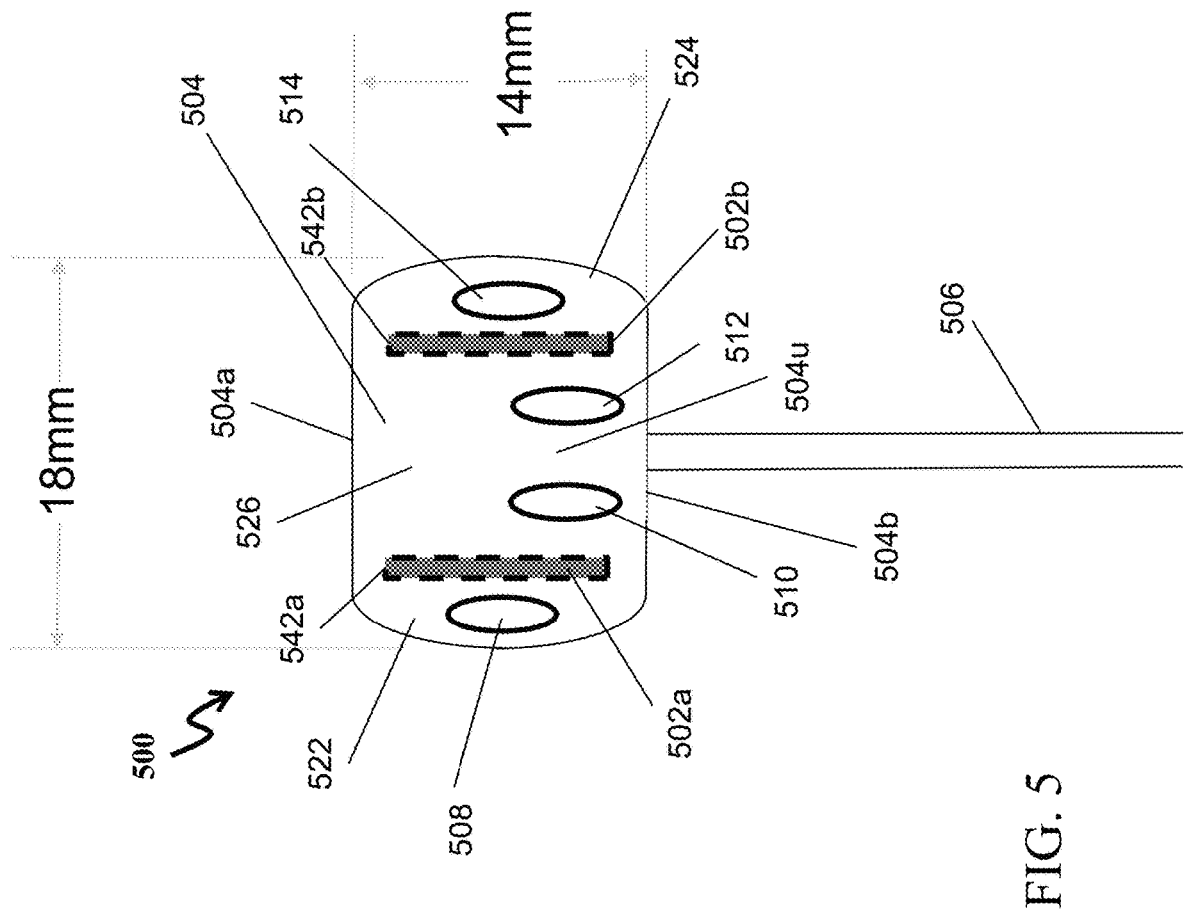
FIG. 5 illustrates a design of an anchor used to cover two surface electrodes in an electrical stimulation lead, in accordance with another embodiment of the present specification.

FIG. 5 illustrates another exemplary design of an electrical stimulation lead arrangement 500, in accordance with an embodiment of the present specification. Arrangement 500 includes a single anchor 504 that is shaped like a rectangle with two opposite and parallel longer edges—a distal longer edge 504a and a proximal longer edge 504b, which are perpendicular to two opposite and parallel shorter edges. In some embodiments, the dimensions of anchor 504 and leads 502a and 502b are the same as or similar to the dimensions of the anchor and electrode shown in FIGS. 1A-1C with the exception of the overall width and length of the anchor as described below. In embodiments, the anchor 504 has a length measured as the distance between the two parallel longer edges 504a and 504b ranging from approximately 10 mm to 20 mm and, in one embodiment, of approximately 14 mm. In an embodiment, the two shorter edges curve outwards away from main body of anchor 504, such as the edges of a semi-circle. The shorter edges are perpendicular to longer edges 504a and 504b. In embodiments, the anchor 504 has a width measured as the distance between the two parallel shorter edges ranging from approximately 12 mm to 24 mm and, in one embodiment, of approximately 18 mm. In embodiments, anchor 504 includes two electrodes 502a and 502b, which are positioned longitudinally on either side of a central axis, parallel and central to the two shorter edges.

Anchor 504 enables anchoring of implantable electrical stimulation lead 500 inside the body of a patient, at the required location, such as on an outer surface of the LES muscle wall. In embodiments, anchor 504 comprises a distal end, corresponding to distal longer edge 504a, and a proximal end, corresponding to proximal longer edge 504b. Proximal longer edge 504b of anchor 504 is coupled with a proximal suture sleeve 506. In embodiments, proximal suture sleeve 506 is connected at a center of proximal longer edge 504b of anchor 504. Suture sleeve 506 may comprise a groove (not shown) in which a suture can be placed for attaching anchor 504 with the patient's tissue.

In embodiments, anchor 504 comprises a first winged portion 522, a second winged portion 524, and a central portion 526. First and second winged portions 522 and 524 are positioned on either sides of central portion 526. In an embodiment, first winged portion comprises first electrode 502a and second winged portion comprises second electrode 502b. Winged portions 522 and 524 merge with each other within central portion 526.

In an embodiment, an upper surface 504u of anchor 504 incorporates two elongated cylindrical structures 542a, 542b, with curved (dome-shaped) edges at its ends. The upper surface 504u is the surface that is positioned on the opposite side of the surface that is eventually in contact with the body tissue of the patient, where electrical stimulation is required. Each elongated cylindrical structure 542a, 542b may be aligned with, house, and cover an outer surface of one of electrodes 502a and 502b. In an embodiment, cylindrical structures 542a, 542b are positioned within winged portions 522 and 524, and are shaped like cylinders of approximately 9 mm in length each.

Lower surface, opposite the upper surface of anchor 504, may include a level/planar surface where electrodes 502a and 502b are attached. Each cylindrical structures 542a, 542b in winged portions 522 and 524 may have a diameter of 2.10 mm.

Located on an outer side, facing the nearest shorter edge, of first electrode 502a, in first winged portion 522, is a first aperture 508. A second aperture 510 is located on the other side of electrode 502a, within first winged portion 522. Similarly, on an outer side of second electrode 502b, in second winged portion 524, is a third aperture 514. A fourth aperture 512 is located on the other side of electrode 502b, within second winged portion 524. In embodiments, all apertures 508, 510, 512, and 514 have oval shapes with a first axis parallel to electrodes 502a and 502b, of approximately 2.1 mm, and second axis perpendicular to the first axis of a length that approximates 1.5 mm. In an embodiment, apertures 510 and 512 mirror each other at identical distances from proximal edge 504a and 504b. In another embodiment, apertures 510 and 512 are at different distances from proximal edge 504b and/or distal edge 504a. In other embodiments, apertures 508, 510, 512, and 514 are circular in shape or oval in shape with first axis parallel to electrodes 502a and 502b that has a length less than a length of a second perpendicular axis. Each aperture allows attaching anchor 504 with patient's tissue by means of a suture.

In embodiments, first and second winged portions 522 and 524 have a thickness in a range of approximately 0.3 to 1.5 mm and, in one embodiment, of approximately 0.9 mm. The curved edges of portions 522 and 524 may transition from the upper surface of anchor 504 to its lower surface in a smooth, curved manner. In some embodiments, an optional distal suture with needle is included and used to hold the anchor in place as the surgeon secures it in place using apertures 508, 510, 512, 514.

In various embodiments of the present specification, described in context of FIGS. 1A to 5, a distal suture is provided through the body tissue. However, the suture does not include electrode(s), which are provided on the surface of the anchor. The sutures enable surgeons to harbor the anchor body to the tissue of the patient. In embodiments, the suture is resorbable within 3-21 days. An example of a suture is a thread manufactured with braided vicryl.

In various embodiments of the present specification, described in context of FIGS. 1A to 5, the proximal suture sleeve (106, 306, 406, 506), may be a 10 mm long tube that is connected to the anchor body. The proximal suture sleeve may provide a thicker section near the anchor to enable placement of a suture, which may be on a groove. In an embodiment, the groove is at a distance of 5 mm at the center of the proximal suture sleeve. The proximal suture sleeve may provide an optional additional means to secure the anchor within the body of the patient.

Figure 6:
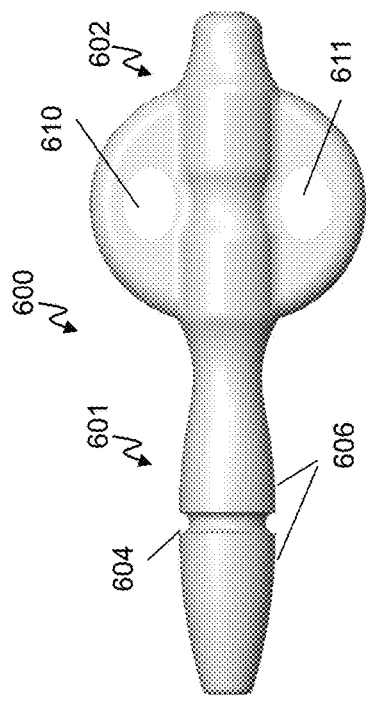
FIG. 6 illustrates an anchor comprising a suture sleeve integrated with a proximal end of an anchoring mechanism, in accordance with some embodiments of the present specification.

FIG. 6 illustrates an anchor 600 comprising a suture sleeve 601 integrated with a proximal end of an anchoring mechanism 602, in accordance with some embodiments of the present specification. Suture sleeve 601 includes a groove 604 to enable placement of a suture. Sleeve 601 is shaped such that it is of greater thickness at the central region 606 of its length, on either sides of groove 604. The greater thickness at the central region 606 allows for a deeper groove 604 which facilitates better holding of a suture placed therein. A less deep groove could easily allow the suture to slip. From the central regions of maximum thickness 606, sleeve 601 gradually thins towards its ends on either sides. Sleeve 601 is symmetrically designed around groove 604. In an embodiment, the anchoring mechanism 602 comprises a butterfly shaped tab with a pair of apertures 610, 611 on opposing sides. When securing the anchor 600 to a patient's tissue, a surgeon may anchor the suture only in the groove 604, only in the butterfly apertures 610, 611, or both in the groove 604 and in the butterfly apertures 610, 611. In some embodiments, an optional distal suture with needle is included and used to hold the anchor in place as the surgeon secures it in place using apertures 610, 611.

Figure 7A:
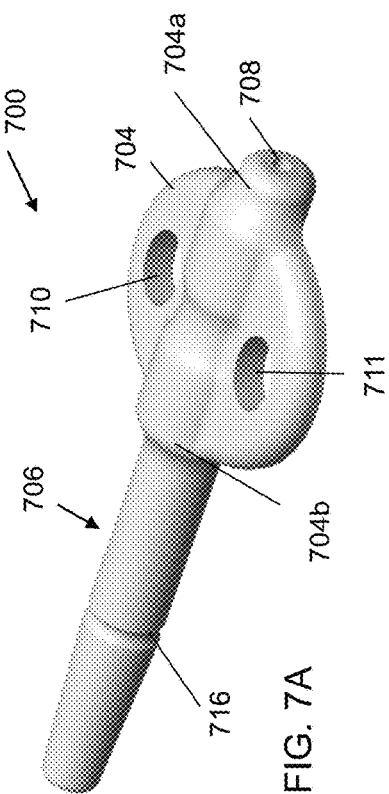
FIG. 7A illustrates a top perspective view of an electrical stimulation lead arrangement or anchor, in accordance with some embodiments of the present specification.
Figure 7B:
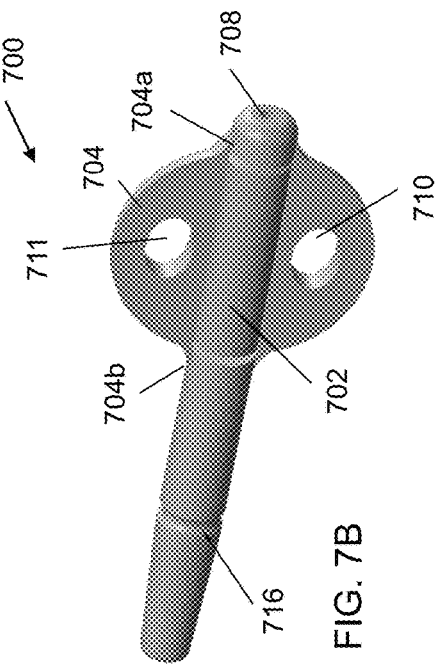
FIG. 7B illustrates a bottom perspective view of the electrical stimulation lead arrangement or anchor of FIG. 7A, in accordance with some embodiments of the present specification.

FIG. 7A illustrates a top perspective view of an electrical stimulation lead arrangement or anchor 700, in accordance with some embodiments of the present specification. FIG. 7B illustrates a bottom perspective view of the electrical stimulation lead arrangement or anchor 700 of FIG. 7A, in accordance with some embodiments of the present specification. Referring simultaneously to FIGS. 7A and 7B, the electrical stimulation lead arrangement or anchor 700 comprises a surface electrode 702 (seen in FIG. 7B) connected to an anchor mechanism 704. A central portion of a proximal end 704b of anchor 704 is connected to a suture sleeve 706. Similar to the embodiment shown in FIG. 6, the anchor 700 of FIGS. 7A and 7B includes a groove 716 placed within a central region 707 of the sleeve 706 having a greater thickness than the remainder of the sleeve 706. In an embodiment, the anchor mechanism 704 comprises a butterfly shaped tab with a pair of apertures 710, 711 on opposing sides. When securing the anchor 700 to a patient's tissue, a surgeon may anchor the suture only in the groove 716, only in the butterfly apertures 710, 711, or both in the groove 716 and in the butterfly apertures 710, 711. In some embodiments, a central portion of a distal end 704a of the anchor mechanism is connected to an optional distal suture. In an embodiment, optional distal suture emerges through a hole 708 in electrode 702. A needle is attached at the distal end of the suture that is brought through hole 708. The optional distal suture is used to hold the butterfly in place as the surgeon secures it in place using apertures 710, 711.

Figures 8A, 8B:
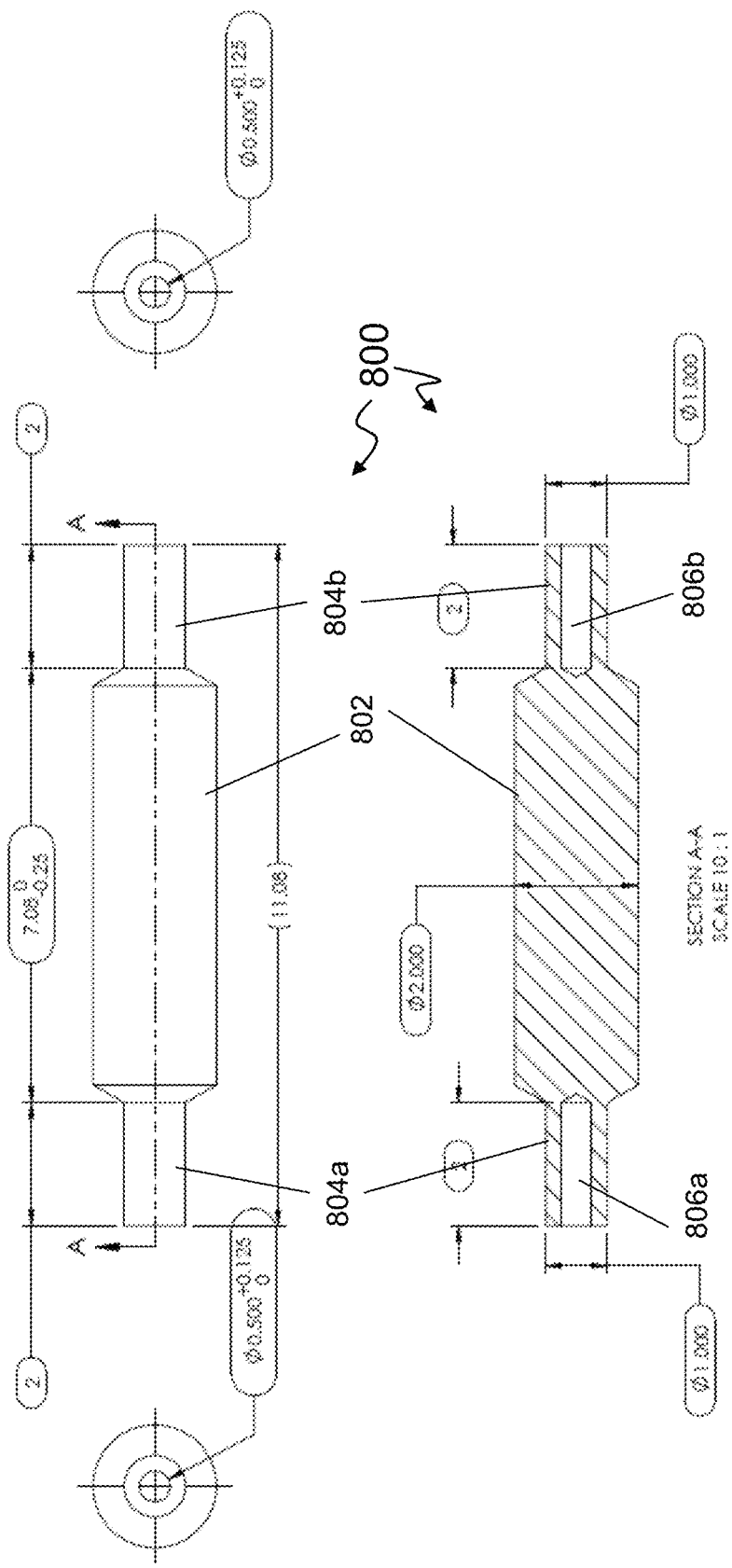
FIG. 8A illustrates an electrode used with an electrical stimulation lead arrangement, in accordance with some embodiments of the present specification.
FIG. 8B illustrates a sectional view of the electrode shown in FIG. 8A, in accordance with some embodiments of the present specification.

FIG. 8A illustrates design of an electrode used with an electrical stimulation lead arrangement, in accordance with some embodiments of the present specification. FIG. 8B illustrates sectional view of design of the electrode shown in FIG. 8A, in accordance with some embodiments of the present specification. Referring simultaneously to FIGS. 8A and 8B, design of surface electrode 800 that is connected to an anchor is shown. In embodiments, electrode 800 is shaped in the form of an elongated cylinder 802 of a first radius, with additional cylinders 804a and 804b of a second radius on either ends of the cylinder of the first radius. In an embodiment, cylinder 804a is at the proximal end of the anchor, and cylinder 804b is at the distal end. The second radius is shorter than the first radius. In an embodiment, the central elongated cylinder 802 has a diameter of approximately 2.00 mm, and a length of approximately 7.08 mm. The shorter and thinner cylindrical structures 804a and 804b, at either ends, may have diameters of approximately 1 mm, and lengths of approximately 2 mm. In embodiments, the anchor covers electrode 800 such that a semi-cylindrical portion of the anchor shields electrode 800 along one portion of the cylindrical surface of electrode 800 along its entire longitudinal axis, while enabling a second portion of the cylindrical surface of electrode 800 to be open for contact with a tissue surface. In some embodiments, the tissue contacting portion of electrode 800 is machined down to be made flat (planar) for better contact with the tissue.

Referring to FIG. 8B, a cylindrical cavity 806*a* is provided within proximal cylinder 804*a*. Similarly, a cylindrical cavity 806*b* is provided within distal cylinder 804*b*. In an embodiment, cylindrical cavities 806*a* and 806*b* have diameters of approximately 0.5 mm. Cavity 806*a* is provided on one side to crimp the lead conductor coils for the electrical stimulation lead. Cavity 806*b* on the other side is provided to crimp an optional distal suture.

Figure 9:
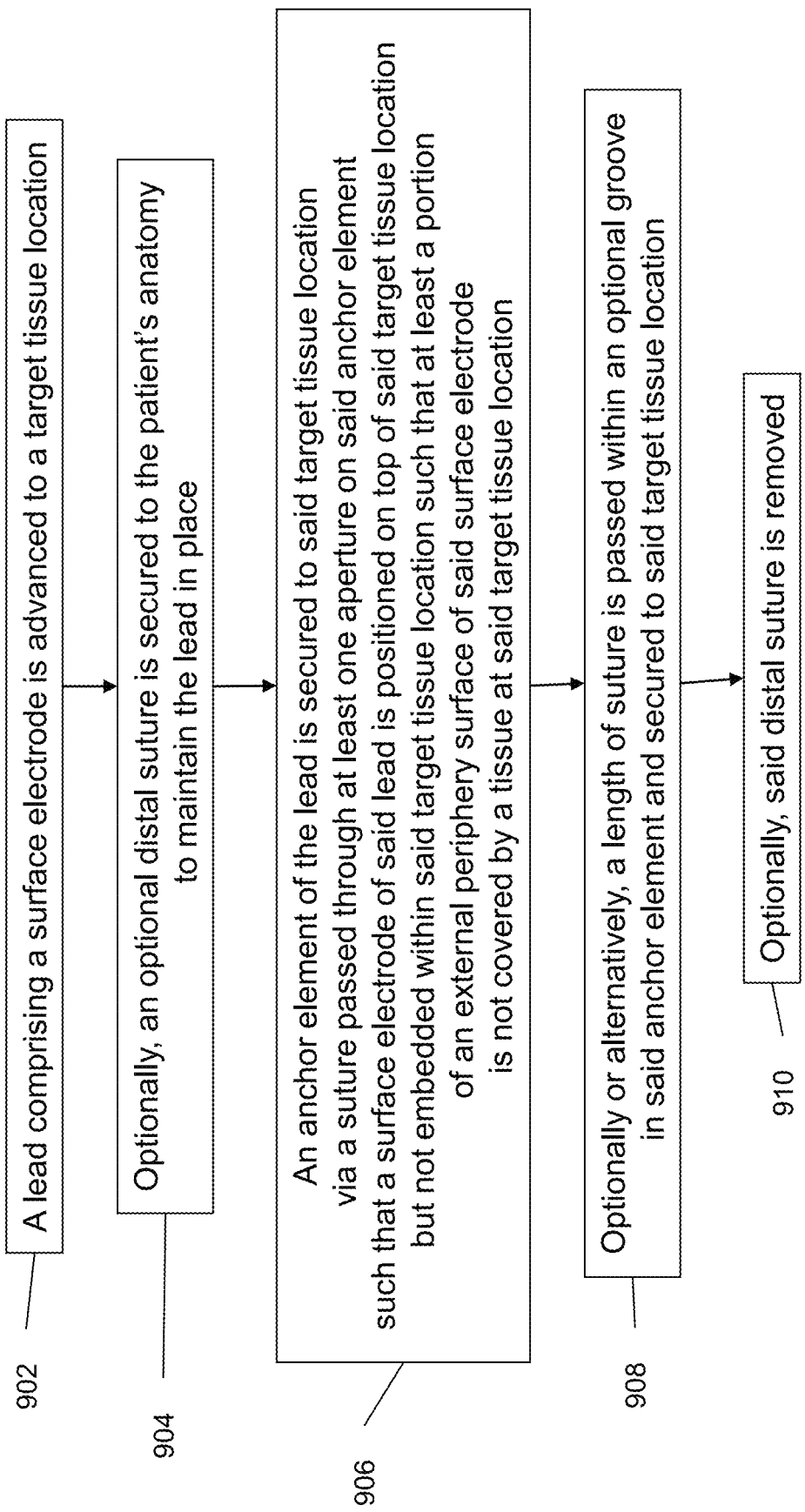
FIG. 9 is a flowchart illustrating a method of implanting a lead comprising a surface electrode in accordance with one embodiment of the present specification.

FIG. 9 is a flowchart illustrating a method of implanting a lead comprising a surface electrode in accordance with one embodiment of the present specification. At step 902, a lead comprising a surface electrode in accordance with the embodiments of the present specification is advanced to a target tissue location. In some embodiments, the target tissue location comprises an area on an outer surface of a lower esophageal sphincter (LES) muscle wall. Optionally, at step 904 an optional distal suture and needle included with the lead and the distal suture is secured to the patient's anatomy, using the needle, to maintain the lead in place. At step 906, an anchor element of the lead is secured to said target tissue location via a suture passed through at least one aperture on said anchor element such that a surface electrode of said lead is positioned on top of said target tissue location but not embedded within said target tissue location such that at least a portion of an external periphery surface of said surface electrode is not covered by a tissue at said target tissue location. Optionally with or alternatively to step 906, at step 908, a length of suture is passed within an optional groove in said anchor element and secured to said target tissue location. Optionally, at step 910, said distal suture secured at step 904 is removed.

The lead design provided by the present specification eliminates the requirement of stitching the electrode into the tissue (LES muscle wall) of a patient, since the electrode being used in the electrical stimulation lead is a surface contacting electrode. The present design reduces surgical time, risk and cost by not requiring the electrodes to be stitched, and hence not requiring an endoscopic check. Further, the use of surface electrodes also eliminates biological pathway for electrode/lead erosion into the lumen of the esophagus. Also, the cost of manufacturing the electrical stimulation lead comprising surface electrodes is less.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An electrical stimulation lead, comprising:
   at least one surface electrode, wherein the at least one surface electrode is configured to be placed on top of a tissue surface in contact with the tissue surface; and
   an anchor coupled to and covering the at least one surface electrode,
   wherein the anchor comprises a distal end and a proximal end, wherein the anchor is defined by two opposing symmetric D-shaped members, each of the two opposing symmetric D-shaped member comprising a straight edge and a curved edge and a central portion attached to the straight edges of each D-shaped member having a length greater than the length of the straight edges, and a distal end cap having a hole axially aligned with the electrode and configured to receive a suture; and
   wherein the surface electrode comprises a distal end having a first width, a proximal end substantially symmetrically opposite to the distal end and having a second width, and a central portion coupling the distal and proximal ends and having a third width, wherein the first and second widths are greater than the third width.

2. The electrical stimulation lead of claim 1, wherein the at least one surface electrode comprises platinum iridium coils.

3. The electrical stimulation lead of claim 1, wherein the anchor comprises silicone.

4. The electrical stimulation lead of claim 1, wherein the anchor further comprises a cylindrical suture sleeve connected to the central portion at the proximal end.

5. The electrical stimulation lead of claim 4, wherein the cylindrical suture sleeve comprises a groove configured to receive a suture.

6. The electrical stimulation lead of claim 1, wherein each of the two opposing symmetric D-shaped members comprises an aperture.

7. The electrical stimulation lead of claim 1, wherein the at least one surface electrode is positioned within the central portion of the anchor.

8. The electrical stimulation lead of claim 1, wherein the at least one surface electrode is of a length greater than the length of the straight edges of each of the two opposing symmetric D-shaped members, and shorter than the length of the central portion.

9. The electrical stimulation lead of claim 1, wherein the at least one surface electrode is of a length shorter than the length of the straight edges of each of the two opposing symmetric D-shaped members.

10. The electrical stimulation lead of claim 1, further comprising a needle at a distal end of the anchor.

11. An electrical stimulation lead, comprising:
    at least one dumbbell shaped surface electrode, wherein the at least one surface electrode is configured to be placed on top of a tissue surface, wherein the at least one surface electrode comprises:
    a central portion having a first width;
    a distal portion having a second width; and
    a proximal portion having a third width, wherein the second width of the distal portion and the third width of the proximal portion are each greater than the first width of the central portion; and
    an anchor coupled to and covering said central, proximal, and distal portions of the at least one surface electrode, along a longitudinal axis of said portions, wherein the anchor comprises a distal end and a proximal end, wherein the anchor is defined by two opposing symmetric D-shaped members, each of the two opposing symmetric D-shaped member comprising a straight edge and a curved edge and a central portion attached to the straight edges of each D-shaped member having a length greater than the length of the straight edges, and a distal end cap having a hole axially aligned with the electrode and configured to receive a suture.

12. The electrical stimulation lead of claim 11, wherein a lower surface of the central portion of the at least one surface electrode is flat and an upper surface of the central portion of the at least one surface electrode is curved.

13. The electrical stimulation lead of claim 11, further comprising a needle at a distal end of the anchor.

* * * * *